US007781639B2

(12) United States Patent
Johnston et al.

(10) Patent No.: US 7,781,639 B2
(45) Date of Patent: *Aug. 24, 2010

(54) MEDICAL ARTICLE HAVING FLUID CONTROL FILM

(75) Inventors: Raymond P. Johnston, Lake Elmo, MN (US); Matthew T. Scholz, Woodbury, MN (US); Steven B. Heinecke, New Richmond, WI (US); Charles A. Hentzen, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 215 days.

This patent is subject to a terminal disclaimer.

(21) Appl. No.: 09/961,091

(22) Filed: Jan. 14, 2002

(65) Prior Publication Data

US 2002/0128578 A1 Sep. 12, 2002

Related U.S. Application Data

(63) Continuation of application No. 09/235,720, filed on Jan. 22, 1999, now Pat. No. 6,420,622, which is a continuation-in-part of application No. 09/099,269, filed on Jun. 18, 1998, now Pat. No. 6,290,685, and a continuation-in-part of application No. 09/099,565, filed on Jun. 18, 1998, now Pat. No. 6,080,243, and a continuation-in-part of application No. 09/106,506, filed on Jun. 18, 1998, now Pat. No. 6,524,488, and a continuation-in-part of application No. 09/100,163, filed on Jun. 18, 1998, now Pat. No. 6,514,412, and a continuation-in-part of application No. 09/099,632, filed on Jun. 18, 1998, now Pat. No. 6,907,921, and a continuation-in-part of application No. 09/099,555, filed on Jun. 18, 1998, now Pat. No. 6,431,695, and a continuation-in-part of application No. 09/099,562, filed on Jun. 18, 1998, now Pat. No. 6,375,871, which is a continuation-in-part of application No. 08/905,481, filed on Aug. 1, 1997, now abandoned.

(51) Int. Cl.
 *A61F 13/00* (2006.01)
(52) U.S. Cl. .......................................... 602/42; 602/52
(58) Field of Classification Search ............. 602/41–59; 604/304–308, 385.1, 383, 387, 358, 378; 428/169, 172, 213, 156, 212, 332, 913; 128/888–889; 424/443–449
See application file for complete search history.

(56) References Cited

U.S. PATENT DOCUMENTS 2,896,618 A * 7/1959 Schaefer ...................... 602/47

(Continued)

FOREIGN PATENT DOCUMENTS

EP 0 051 935 5/1982

(Continued)

OTHER PUBLICATIONS

Article: "Fabrication of Novel Three-Dimensional Microstructures by the Anisotropic Etching of (100) and (110) Silicon", Ernest Bassous, *IEEE Transactions on Electron Devices*, vol. ED-25, No. 10, Oct. 1978.
Article: "Microtechnology Opens Doors to the Universe of Small Space", Peter Zuska *Medical Device & Diagnostic Industry*, Jan. 1997.

(Continued)

*Primary Examiner*—Michael A. Brown
(74) *Attorney, Agent, or Firm*—Michael G. Williams

(57) ABSTRACT

The present invention provides medical articles having a fluid control film component which comprise a sheet having microchannels that permit directional flow of a liquid. Articles incorporating the fluid control film include: wound dressings, wound drains, tympanostomy fluid wicks, intravenous access site dressings, drug delivery dressings, and sweat collection patches.

10 Claims, 12 Drawing Sheets

U.S. PATENT DOCUMENTS

| | | | |
|---|---|---|---|
| 2,915,554 A | | 12/1959 | Ahlbrecht et al. |
| RE24,906 E | | 12/1960 | Ulrich |
| 3,389,827 A | | 6/1968 | Abere et al. |
| 3,715,192 A | | 2/1973 | Wenz et al. |
| 3,921,627 A | | 11/1975 | Wilson et al. |
| 3,993,566 A | | 11/1976 | Goldberg et al. |
| 4,112,213 A | | 9/1978 | Waldman |
| 4,233,029 A | | 11/1980 | Columbus |
| 4,271,119 A | | 6/1981 | Columbus |
| 4,277,966 A | | 7/1981 | Rambauske |
| 4,310,509 A | | 1/1982 | Berglund et al. |
| 4,323,069 A | | 4/1982 | Ahr et al. |
| 4,323,557 A | | 4/1982 | Rosso et al. |
| 4,379,454 A | * | 4/1983 | Campbell et al. ............ 424/448 |
| 4,413,407 A | | 11/1983 | Columbus |
| 4,439,391 A | | 3/1984 | Hung |
| 4,472,480 A | | 9/1984 | Olson |
| 4,485,809 A | | 12/1984 | Dellas |
| 4,579,555 A | | 4/1986 | Russo |
| 4,600,001 A | | 7/1986 | Gilman |
| 4,601,861 A | | 7/1986 | Pricone et al. |
| 4,639,748 A | | 1/1987 | Drake et al. |
| 4,668,558 A | | 5/1987 | Barber |
| 4,737,410 A | | 4/1988 | Kantner |
| 4,758,481 A | | 7/1988 | Fauvel |
| 4,803,078 A | | 2/1989 | Sakai |
| 4,871,812 A | | 10/1989 | Lucast et al. |
| 4,906,439 A | | 3/1990 | Grenner |
| 4,913,858 A | | 4/1990 | Miekka et al. |
| 4,950,549 A | | 8/1990 | Rolando et al. |
| 4,961,985 A | | 10/1990 | Henn et al. |
| 5,038,798 A | * | 8/1991 | Dowdy et al. ............... 128/853 |
| RE33,727 E | | 10/1991 | Sims |
| 5,069,403 A | | 12/1991 | Marentic et al. |
| 5,078,925 A | | 1/1992 | Rolando et al. |
| 5,125,401 A | | 6/1992 | Gerhartl |
| 5,133,516 A | | 7/1992 | Marentic et al. |
| 5,158,557 A | | 10/1992 | Noreen et al. |
| 5,161,544 A | | 11/1992 | Morris |
| 5,175,030 A | | 12/1992 | Lu et al. |
| 5,200,248 A | | 4/1993 | Thompson et al. |
| 5,225,473 A | | 7/1993 | Duan |
| 5,249,359 A | | 10/1993 | Schubert et al. |
| 5,268,213 A | | 12/1993 | Murakami et al. |
| 5,314,743 A | | 5/1994 | Meirowitz et al. |
| 5,336,209 A | | 8/1994 | Porzilli |
| 5,376,252 A | | 12/1994 | Ekstrom et al. |
| 5,411,858 A | | 5/1995 | McGeehan et al. |
| 5,440,332 A | | 8/1995 | Good |
| 5,450,235 A | | 9/1995 | Smith et al. |
| 5,468,821 A | | 11/1995 | Lucast et al. |
| 5,474,527 A | | 12/1995 | Bettinger |
| 5,474,824 A | | 12/1995 | Martakos et al. |
| 5,514,120 A | * | 5/1996 | Johnston et al. ............. 604/378 |
| 5,585,186 A | | 12/1996 | Scholz et al. |
| 5,591,820 A | | 1/1997 | Kydonieus et al. |
| 5,609,624 A | | 3/1997 | Kalis |
| 5,632,731 A | * | 5/1997 | Patel ........................... 602/59 |
| 5,651,888 A | | 7/1997 | Shimizu et al. |
| 5,691,846 A | | 11/1997 | Benson, Jr. et al. |
| 5,728,446 A | | 3/1998 | Johnston et al. |
| 5,738,642 A | | 4/1998 | Heinecke et al. |
| 5,807,295 A | | 9/1998 | Hutcheon et al. |
| 5,853,750 A | | 12/1998 | Dietz et al. |
| 5,895,380 A | * | 4/1999 | Turi et al. ................... 604/383 |
| 5,932,315 A | | 8/1999 | Lum et al. |
| 6,080,243 A | | 6/2000 | Insley et al. |
| 6,238,583 B1 | | 5/2001 | Parce et al. ................. 204/600 |
| 6,240,790 B1 | | 6/2001 | Swedberg et al. ........ 73/863.21 |
| 6,290,685 B1 | | 9/2001 | Insley et al. |
| 6,420,622 B1 | * | 7/2002 | Johnston et al. ............... 602/41 |
| 6,613,560 B1 | | 9/2003 | Tso et al. |

FOREIGN PATENT DOCUMENTS

| | | | |
|---|---|---|---|
| EP | 0 872 330 A1 | 10/1998 | |
| FR | 2 433 935 | 3/1980 | |
| FR | 2 662 361 | 5/1990 | |
| GB | 1 338 579 | 11/1973 | |
| GB | 1 354 502 | 5/1974 | |
| GB | 2 294 426 | 5/1996 | |
| WO | WO 91/12949 | 9/1991 | |
| WO | WO 93/11727 | 6/1993 | |
| WO | WO 96/03094 | 2/1996 | |
| WO | WO 96/09879 | 4/1996 | |
| WO | WO 97/09017 | 3/1997 | |
| WO | WO 97/13633 | 4/1997 | |

OTHER PUBLICATIONS

Article: Fabrication of Microstructures with high aspect ratios and great structural heights by synchrotron radition lithography, galvanoforming, and plastic moulding (LIGA) Becker, et al. *MiMicroelecctronic Engineering* 4 (1986).

Article: "Processing of Three-Dimensional Microstructures Using Macroporous n-Type Silicon" Ottow et al. *J. Electrochem. Soc.*, vol. 143, No. 1, Jan. 1996.

U.S. Appl. No. 09/099,269, filed Jun. 18, 1998, entitled "Microchanneled Active Fluid Transport Devices".

U.S. Appl. No. 09/099,555, filed Jun. 18, 1998, entitled "Microstructure Liquid Dispenser".

U.S. Appl. No. 09/099,562, filed Jun. 18, 1998, entitled "Microfluidic Articles and Method of Manufacturing Same".

U.S. Appl. No. 09/099,632, filed Jun. 18, 1998, entitled "Microchanneled Active Fluid Heat Exchanger".

U.S. Appl. No. 09/100,163, filed Jun. 18, 1998, entitled "Microstructured Separation Device".

U.S. Appl. No. 09/106,506, filed Jun. 18, 1998, entitled "Structured Surface Filtration Media".

* cited by examiner

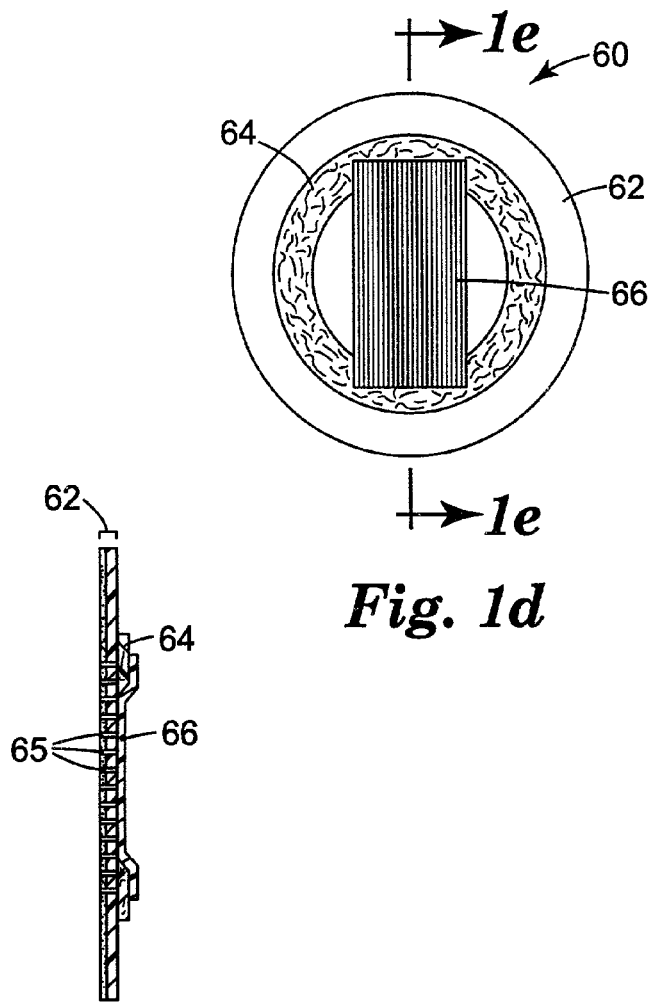
Fig. 1d
Fig. 1e
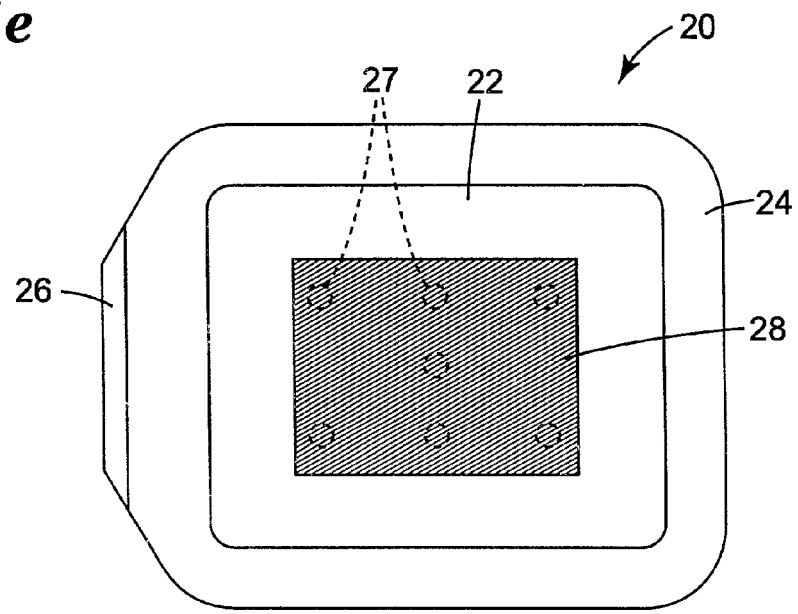
Fig. 1g

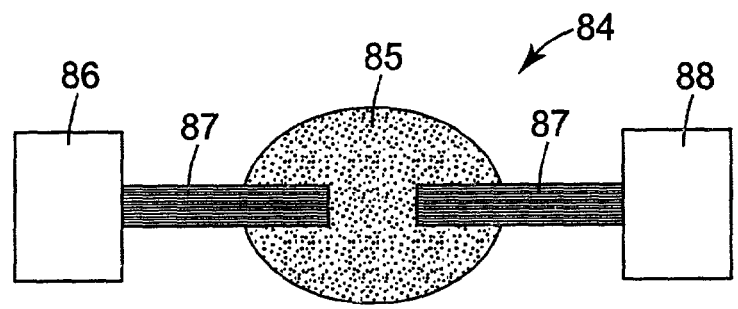
*Fig. 2g*
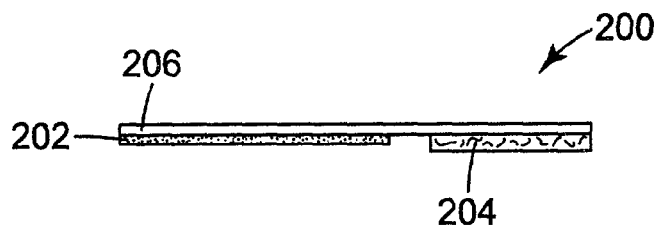
*Fig. 2h*
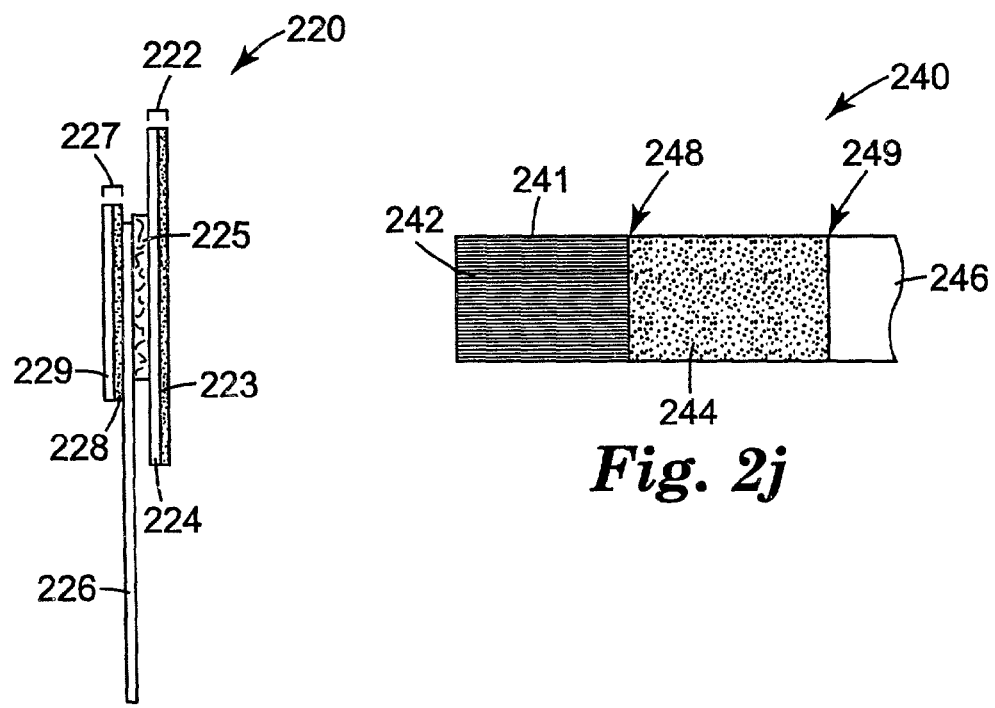
*Fig. 2i*
*Fig. 2j*

MEDICAL ARTICLE HAVING FLUID CONTROL FILM

This application is a continuation of U.S. Ser. No. 09/235,720, filed Jan. 22, 1999 now U.S. Pat. No. 6,420,622, which is a continuation-in-part of Ser. No. 09/099,269, filed Jun. 18, 1998 now U.S. Pat. No. 6,290,685; Ser. No. 09/099,565, filed Jun. 18, 1998 now U.S. Pat. No. 6,080,243; Ser. No. 09/106,506, filed Jun. 18, 1998 now U.S. Pat. No. 6,524,488; Ser. No. 09/100,163, filed Jun. 18, 1998 now U.S. Pat. No. 6,514,412; Ser. No. 09/099,632, filed Jun. 18, 1998 now U.S. Pat. No. 6,907,921; Ser. No. 09/099,555, filed Jun. 18, 1998 now U.S. Pat. No. 6,431,695; and Ser. No. 09/099,562, filed Jun. 18, 1998 now U.S. Pat. No. 6,375,871, which is a continuation-in-part of U.S. Ser. No. 08/905,481, filed Aug. 1, 1997 now abandoned.

FIELD OF THE INVENTION

This invention relates to articles that have the capability to control or transport fluids, especially biological fluids. In one embodiment this invention relates to medical wound dressings and drains and intravenous access site dressings.

BACKGROUND OF THE INVENTION

The control and/or transport of biological fluids poses many problems at different stages in treatment or diagnosis processes. During surgery, steps are undertaken in an effort to control and/or transport the fluids that result from the surgery. In some instances these fluids are needed to be recycled back to the patient. For example, vital blood lost from the patient may be returned in emergency situations. In other instances fluids must be controlled so that an aseptic and safe operating room environment is maintained. It is often times desired, for example, to avoid spillage of fluids onto the operating room floor where it would create an unsafe situation and mess. After surgery, the need to control and/or transport fluids remains. For example, wound exudate can pose problems in the treatment and care of the wound site and needs to be handled. Also, the delivery of fluid medicaments to a wound site can present challenges.

Several surgical drapes and pouches have been designed in an attempt to control fluids generated during surgery. Many of these devices utilize absorbent padding or plastic pouches to collect the fluid. In many situations, however, there does not exist enough room at the site where the fluid is emanating from to adequately control the fluid.

Suction tubes, optionally connected to a central vacuum line or remote vacuum source, may also be employed to collect fluids from a wound site. These tubes have a significant number of limitations that inhibit the desired management of the fluid. For example, post operative wound drain tubes create significant patient discomfort and can be a source of infection. Furthermore, many wounds require multiple drain tubes.

In the treatment of many wounds it is beneficial to keep the wound moist while removing excess exudate. This environment provides an optimum wound healing environment, reduces pain, and provides an environment for autolytic debridement and re-epilethlialization. Excess fluid, however, can lead to problems such as maceration (skin breakdown) and microbial infection of the wound site. For this reason, many wound dressings are sometimes designed to have absorbent pads and/or high moisture vapor transmission rates (hereinafter "MVTR"), i.e. the excess fluid is allowed to transmit or evaporate through the wound dressing.

Fluid can be a particular problem when dealing with highly exuding wounds, IV sites, as well as sites for gastric (G), jejunostomy (J) and nasal gastric (NG) tubes. For example, many commercially available intravenous access site dressings (hereinafter "I.V. Dressings") do not have sufficient MVTR to permit rapid evaporation of moisture through the dressing. Consequently, in some instances this can result in fluid pockets forming beneath the dressing around the puncture site. This fluid can result in one or more problems such as "bandage lift" (which reduces the ability of the bandage to secure the IV line to the skin), skin maceration, or bacterial infection.

A stated advantage to certain of these dressings is transparency of part or all of the dressing. This allows for direct visual observation of the wound healing progress. For example, thin film adhesive coated dressing having a site revealing "window" surrounded by an absorbent such as a hydrocolloid have been tried. Unfortunately, however, these dressings require that the "window" be relatively small to ensure that the fluid be in sufficient direct contact with the absorbent to prevent fluid build up. Even so, these small dressings may not absorb fluid rapidly enough to prevent fluid build up around the IV puncture site.

Alternatively, attempts have been made to place a gauze absorbent or an "island dressing" (i.e., a dressing having an "island" of absorbent fabric or hydrophilic foam contained therein) directly over the wound. Island dressings are able rapidly to absorb fairly high amounts of wound exudate and, therefore, are useful for highly exuding wounds. Unfortunately, however, the presence of the absorbent directly over the wound prevents visual observation of wound healing. Finally, certain transparent hydrocolloid dressings are also available that absorb the fluid into a polymeric matrix. These dressings can absorb large volumes of fluid but generally the absorption is not very rapid and hydrocolloids tend to break down in the wound.

Drug delivery dressings have been developed that contain a reservoir of a suitable medicament. The reservoir is placed in contact with the skin and the medicament is allowed or assisted to permeate the skin. Unfortunately, the amount of drug contained within the dressing is limited for a particular size of dressing and these dressings do not have a capability to be recharged from a remote reservoir. Many of these dressings are not suitable for application over open wounds. For example, many transdermal drug delivery devices rely on the barrier provided by the dermis to regulate drug delivery rate.

Otitis media, inflammation of the middle ear, accounts for more visits to pediatricians than any other illness. Otitis media is generally regarded as a complication of eustachian tube dysfunction. The normal eustachian tube is closed, except during swallowing, when it allows pressure equalization between the middle ear and nasopharynx. When it does not close properly, due to inflammation due to a cold, for example, the eustachian tube can act as a conduit for movement of bacteria into the middle ear from the nose. Gram-positive microorganisms, most prevalently *S. pneumoniae* and *S. pyogenes*, constitute the bacterial origin of otitis media. Furthermore, if the eustachian tubes are subsequently blocked so that negative pressure develops inside the middle ear, serum may leave the blood vessels in the middle ear under hydrostatic pressure and accumulate there, a condition known as otitis media with effusion.

Treatment of otitis media involves observation and antibiotic therapy, and for infections that persist, surgical placement of ear tubes. Antibiotic treatment of otitis media involves systemic administration of antibiotics such as amoxicillin. Increasingly, the use of antibiotic therapy for treatment of this disease is coming into question due to knowledge that widespread use of antibiotics allows for selection of resistant strains of bacteria. However, most physicians continue to prescribe antibiotics because it is difficult to predict which patients will get well without treatment and which will proceed to chronic otitis media and potentially fatal sequelae such as meningitis.

Installation of ear tubes is another treatment for otitis media. The tubes are grommets that are placed in the tympanic membrane so that a ventilation hole is maintained for fluid to escape from the middle ear. Occasionally, ear tubes are removed by the surgeon after the infection has cleared. More frequently, the ear tubes fall out of the ear after the infection has resolved. In either case, the tympanic membrane usually (in 60-70% of cases) heals with little or no hearing dysfunction. An unresolved problem with current ear tube designs is that they may fall out before the ear infection has resolved; this occurs in up to 25% of cases, increasing total cost of treating otitis media.

Suction tubes have been used in dentistry to help control and remove fluids from the oral cavity. Generally these tubes are pretty simple devices. Unfortunately, however, the tubes in use suffer from some drawbacks. First, they can be very noisy, causing the patient, dentist and/or assistant to become agitated or annoyed. Second, they generally suck fluid from only one point in the cavity. To remove fluid from other areas the tube must be manually repositioned. Moreover, positioning the tube into small openings or isolating individual teeth or regions is precluded. Additionally, there have been reported cases of cross contamination from patient to patient, caused from a malfunction of the suction pump. Finally, the tube is prone to getting blocked by the tissue.

From the foregoing, it will be appreciated that what is needed in the art are articles having a built in capability to control or transport fluids, especially biological fluids. In the case of surgical drape articles, there is a great need for articles that can control or transport fluids emanating from a surgical site. In the case of medical treatment articles (e.g., wound dressings), there is a great need for dressings that keep the wound area at a preferred moisture level, articles that are capable of transporting fluid between the wound site and a remote area, or are capable of delivering a medicament to a wound site. It would be a further advancement in the art to provide such articles in a reliable and low cost manner. Such articles and methods for preparing the same are disclosed and claimed herein.

SUMMARY OF THE INVENTION

The present invention provides fluid control or transport articles comprising at least one fluid control film component which comprises a sheet having at least one microstructure-bearing surface with one or more channels therein that permits, promotes, or facilitates control or directional flow of a liquid. Medical treatment articles containing a fluid control film component are provided.

In one embodiment, this invention relates to novel surgical drapes that incorporate a fluid control film. The fluid control film may be incorporated to transport a fluid to a remote site (e.g., facilitate wicking of a fluid away from an operating site and out of the way of the surgeon), deliver a fluid to a site (e.g., facilitate delivery of a medicament or flushing solution to a surgery site), or absorb or contain excess wound exudate.

In another embodiment, this invention relates to novel wound dressings that incorporate at least one fluid control film. The fluid control film may be incorporated to transport a fluid to a remote site, deliver a fluid to a site, disperse the fluid over an increased surface area to promote more rapid evaporation (e.g., through a high MVTR film), or absorb excess wound exudate. The dressings may be fabricated to accommodate wounds of all types, including: burns, abrasions, surgical wounds, lacerations, etc.

The topical wound dressing of one preferred embodiment transports (e.g., wicks) fluid off wounds by capillary action to a remote storage reservoir. This embodiment functions in an opposite manner to conventional wound dressings that place an absorbent over the wound itself. Dressings of this embodiment are preferably able to provide one or more of the following benefits:

1) wound moisture level optionally may be adjusted by modification of the surface topography and/or surface energy of the fluid wick in combination with the MVTR of the dressing;
2) the dressing is optionally and preferably transparent and allows visual inspection of the wound site; and
3) an optional absorbent may be isolated or positioned remote from the wound site, thereby absorbing excess exudate while allowing direct visualization of the wound. The absorbent is preferably covered with a permeable film, thus enabling the healthy tissue surrounding the wound not to be in contact with excess wound exudate.

The fluid transportation or "wicking" property may be provided by fluid control film incorporating a microreplicated pattern. The pattern may be provided in the backing or adhesive layer of a dressing, or by a separate piece of film. The storage reservoir is preferably a hydrophilic fabric such as a woven, knit, or non-woven, a hydrocolloid, foam, or a gel system that is able to absorb large amounts of fluid exudate. Preferably a high MVTR transparent or translucent backing is used. Certain dressings may also be used to supply medicaments to the wound such as antimicrobials, antibiotics, growth factors, irrigation fluid, anesthetics/analgesics, and the like. Certain other dressings may incorporate the optional medicaments directly into the adhesive, film backing, or microreplicated fluid transport wick.

In another embodiment, drug delivery dressings are provided. The delivery dressings incorporate fluid control film component to facilitate delivery of a medicament to the skin.

In another embodiment, the present invention provides a novel treatment for otitis media that utilizes novel tympanostomy wicks or tubes and/or a medicament (e.g., an antibacterial agent, preferably one that is covalently attached to the tympanostomy article or placed in the inner ear by means of a syringe through the article itself). The novel wick or tube design utilizes microreplication to produce microchannels that transport fluid, e.g., by capillary action. Preferred designs also incorporate macrochannels to allow drainage of highly viscous fluid that cannot be removed by capillary forces.

In another embodiment, dental suction devices are provided that comprise a fluid control film.

BRIEF DESCRIPTION OF THE DRAWINGS

The invention may be more clearly understood by reference to the drawings, wherein:

FIGS. 1a-1g illustrate various medical dressings of the present invention;

FIGS. 2a-2j illustrate additional medical dressings and medical wound drains of the present invention;

Figure 1A:
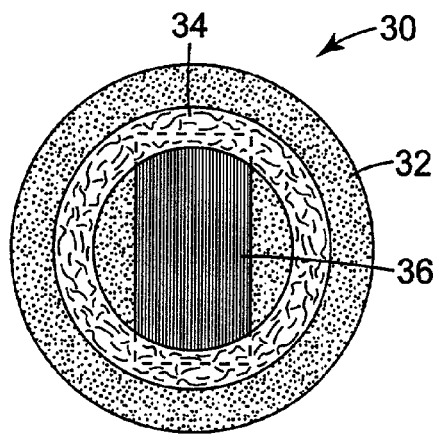

These figures, which are idealized, are not to scale and are intended to be merely illustrative and non-limiting.

DEFINITIONS

Unless otherwise specified, the following terms should be construed in accordance with the following definitions:

Fluid Control Film ("FCF") refers to a film or sheet or layer having at least one major surface comprising a microreplicated pattern capable of manipulating, guiding, containing, spontaneously wicking, transporting, or controlling, a fluid.

Fluid Transport Film ("FTF") refers to a film or sheet or layer having at least one major surface comprising a microreplicated pattern capable of spontaneously wicking or transporting a fluid.

"Microreplication" means the production of a microstructured surface through a process where the structured surface features retain an individual feature fidelity during manufacture.

DETAILED DESCRIPTION OF THE INVENTION

The present invention relates to articles that incorporate a fluid control film component. At the beginning of this section suitable fluid control films will be described generally. Descriptions of illustrative articles incorporating these films will follow.

Suitable fluid control films for use in the present invention are described in U.S. Pat. Nos. 5,514,120; 5,728,446, 6,080, 243; and 6,290,685. Preferred fluid control films of the invention are in the form of sheets or films rather than a mass of fibers. The channels of fluid control films of the invention preferably provide more effective liquid flow than is achieved with webs, foam, or tows formed from fibers. The walls of channels formed in fibers will exhibit relatively random undulations and complex surfaces that interfere with flow of liquid through the channels. In contrast, the channels in the present invention are precisely replicated from a predetermined pattern and form a series of individual open capillary channels that extend along a major surface. These microreplicated channels formed in sheets, films, or tubes are preferably uniform and regular along substantially each channel length and more preferably from channel to channel.

Certain of the fluid control films of the present invention are capable of spontaneously and uniformly transporting liquids along the axis of the film channels. Two general factors that influence the ability of fluid control films to spontaneously transport liquids (e.g., water, urine or vaginal secretions) are (i) the geometry or topography of the surface (capillarity, shape of the channels) and (ii) the nature of the film surface (e.g., surface energy). To achieve the desired amount of fluid transport capability the designer may adjust the structure or topography of the fluid control film and/or adjust the surface energy of the fluid control film surface. In order for a closed channel wick made from a fluid control film to function it preferably is sufficiently hydrophilic to allow the desired fluid to wet the surface. Generally, to facilitate spontaneous wicking in open channels, the fluid must wet the surface of the fluid control film, and the contact angle be equal or less than 90 degrees minus one-half the notch angle.

The channels of fluid control films of the present invention can be of any geometry that provides desired liquid transport, and preferably one that is readily replicated.

The invention fluid control films can be formed from any thermoplastic materials suitable for casting, or embossing including, for example, polyolefins, polyesters, polyamides, poly(vinyl chloride), polyether esters, polyimides, polyesteramide, polyacrylates, polyvinylacetate, hydrolyzed derivatives of polyvinylacetate, etc., or combinations thereof. Polyolefins are preferred, particularly polyethylene or polypropylene, blends and/or copolymers thereof, and copolymers of propylene and/or ethylene with minor proportions of other monomers, such as vinyl acetate or acrylates such as methyl and butylacrylate. Polyolefins are preferred because of their excellent physical properties, ease of processing, and typically lower cost than other thermoplastic materials having similar characteristics. Polyolefins readily replicate the surface of a casting or embossing roll. They are tough, durable and hold their shape well, thus making such films easy to handle after the casting or embossing process. Hydrophilic polyurethanes are also preferred for their physical properties and inherently high surface energy. Alternatively, fluid control films can be cast from thermosets (curable resin materials) such as polyurethanes, acrylates, epoxies and silicones, and cured by exposure to heat or UV or E-beam radiation, or moisture. These materials may contain various additives including surface energy modifiers (such as surfactants and hydrophilic polymers), plasticizers, antioxidants, pigments, release agents, antistatic agents and the like. Suitable fluid control films also can be manufactured using pressure sensitive adhesive materials. In some cases the channels may be formed using inorganic materials (e.g., glass, ceramics, or metals). Preferably, the fluid control film substantially retains its geometry and surface characteristics upon exposure to liquids. The fluid control film may also be treated to render the film biocompatible. For example, a heparin coating may be applied.

Generally, the susceptibility of a solid surface to be wet out by a liquid is characterized by the contact angle that the liquid makes with the solid surface after being deposited on the horizontally disposed surface and allowed to stabilize thereon. It is sometimes referred to as the "static equilibrium contact angle", sometimes referred to herein merely as "contact angle".

Figure 8A:
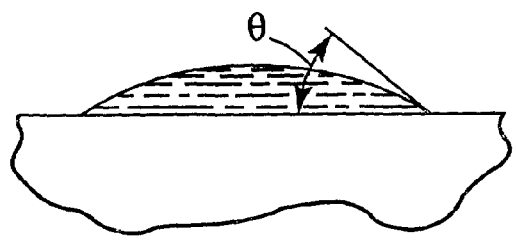
FIGS. 8a and 8b are schematic diagrams used to illustrate interaction of a liquid on a surface.
Figure 8B:
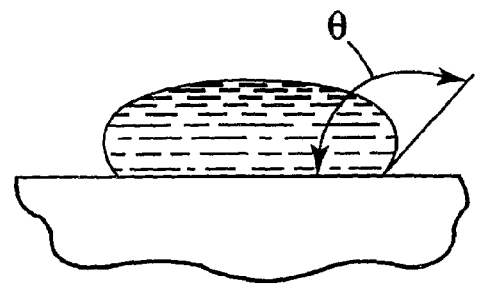

As shown in FIGS. 8a and 8b, the contact angle Theta is the angle between a line tangent to the surface of a bead of liquid on a surface at its point of contact to the surface and the plane of the surface. A bead of liquid whose tangent was perpendicular to the plane of the surface would have a contact angle of 90°. Typically, if the contact angle is 90° or less, as shown in FIG. 8a, the solid surface is considered to be wet by the liquid. Surfaces on which drops of water or aqueous solutions exhibit a contact angle of less than 90° are commonly referred to as "hydrophilic". As used herein, "hydrophilic" is used only to refer to the surface characteristics of a material, i.e., that it is wet by aqueous solutions, and does not express whether or not the material absorbs aqueous solutions. Accordingly, a material may be referred to as hydrophilic whether or not a sheet of the material is impermeable or permeable to aqueous solutions. Thus, hydrophilic films used in fluid control films of the invention may be formed from films prepared from resin materials that are inherently hydrophilic, such as for example, poly(vinyl alcohol). Liquids that yield a contact angle of near zero on a surface are considered to completely wet out the surface. Polyolefins, however, are typically inherently hydrophobic, and the contact angle of a polyolefin film, such as polyethylene or polypropylene, with water is typically greater than 90°, such as shown in FIG. 8b.

Depending on the nature of the microreplicated film material itself, and the nature of the fluid being transported, one may desire to adjust or modify the surface of the film in order to ensure sufficient capillary forces of the article. For example, the surface of the fluid control film may be modified in order to ensure it is sufficiently hydrophilic. Body liquids that will come into contact with the fluid control films of the present invention are aqueous. Thus, if such films are used as fluid control films of the invention, they generally must be modified, e.g., by surface treatment, application of surface coatings or agents, or incorporation of selected agents, such that the surface is rendered hydrophilic so as to exhibit a contact angle of 90° or less, thereby enhancing the wetting and liquid transport properties of the fluid control film. Suitable methods of making the surface hydrophilic include: (i) incorporation of a surfactant; (ii) incorporation or surface coating with a hydrophilic polymer; and (iii) treatment with a hydrophilic silane. Other methods are also envisioned.

The fluid control films of the invention may have a variety of topographies. Preferred fluid control films are comprised of a plurality of channels with V-shaped or rectangular cross-sections, and combinations of these, as well as structures that have secondary channels, i.e., channels within channels. For open channels, the desired surface energy of the microstructured surface of V-channeled fluid control films is such that:

$$\text{Theta} \leq (90° - \text{Alpha}/2),$$

wherein Theta is the contact angle of the liquid with the film and Alpha ($\alpha$) is the average included angle of the secondary V-channel notches. (See, e.g., FIG. 6g).

Any suitable known method may be utilized to achieve a hydrophilic surface on fluid control films of the present invention. Surface treatments may be employed such as topical application of a surfactant, plasma treatment, vacuum deposition, polymerization of hydrophilic monomers, grafting hydrophilic moieties onto the film surface, corona or flame treatment, etc. Alternatively, a surfactant or other suitable agent may be blended with the resin as an internal additive at the time of film extrusion. It is typically preferred to incorporate a surfactant in the polymeric composition from which the fluid control film is made rather than rely upon topical application of a surfactant coating. Topically applied coatings tend to fill in, i.e., blunt, the notches of the channels, thereby interfering with the desired liquid flow to which the invention is directed. An illustrative example of a surfactant that can be incorporated in polyethylene fluid control films is TRITON™ X-100, an octylphenoxypolyethoxyethanol nonionic surfactant, e.g., used at between about 0.1 and 0.5 weight percent.

An illustrative method for surface modification of the films of the present invention is the topical application of a 1 percent aqueous solution of the reaction product comprising 90 weight percent or more of:

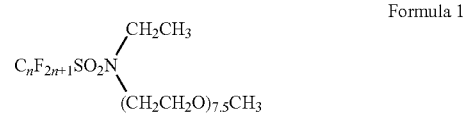

Formula 1 wherein n=8 (97 percent), n=7 (3 percent), and 10 weight percent or less of:

$$C_nF_{2n+1}SO_2N\begin{matrix}CH_2CH_3\\H\end{matrix}$$

Formula 2 wherein n=8 (97 percent), n=7 (3 percent). Preparation of such agents is disclosed in U.S. Pat. No. 2,915,554 (Ahlbrecht et al.)

As discussed above, a surfactant or mixture of surfactants may be applied to the surface of the fluid control film or impregnated into the article in order to adjust the properties of the fluid control film or article. For example, it may be desired to make the surface of the fluid control film more hydrophilic than the film would be without such a component.

Preferred embodiments of the present invention retain the desired fluid transport properties throughout the life of the product into which the fluid control film is incorporated. In order to ensure the surfactant is available throughout the life of the fluid control film the surfactant preferably is available in sufficient quantity in the article throughout the life of the article or is immobilized at the surface of the fluid control film. For example, a hydroxyl functional surfactant can be immobilized to a fluid control film by functionalizing the surfactant with a di- or tri-alkoxy silane functional group. The surfactant could then be applied to the surface of the fluid control film or impregnated into the article with the article subsequently exposed to moisture. The moisture would result in hydrolysis and subsequent condensation to a polysiloxane. Hydroxy functional surfactants (especially 1,2 diol surfactants) may also be immobilized by association with borate ion. Suitable surfactants include anionic, cationic, and nonionic surfactants, however, nonionic surfactants may be preferred due to their relatively low irritation potential. Polyethoxylated and polyglucoside surfactants are particularly preferred including polyethoxylated alkyl, aralkyl, and alkenyl alcohols, ethylene oxide and propylene oxide copolymers such as "Pluronic" and "Tetronic", alkylpolyglucosides, polyglyceryl esters, and the like. Other suitable surfactants are disclosed in U.S. Ser. No. 08/576,255.

As discussed above, a hydrophilic polymer or mixture of polymers may be applied to the surface of the fluid control film or impregnated into the article in order to adjust the properties of the fluid control film or article. In order to ensure the hydrophilic polymer is available throughout the life of the fluid control film the polymer preferably is available in sufficient quantity in the article throughout the life of the article or is immobilized at the surface of the fluid control film. Alternatively, a hydrophilic monomer may be added to the article and polymerized in situ to form an interpenetrating polymer network. For example, a hydrophilic acrylate and initiator could be added and polymerized by heat or actinic radiation.

Suitable hydrophilic polymers include: homo- and co-polymers of ethylene oxide; hydrophilic polymers incorporating vinyl unsaturated monomers such as vinylpyrrolidone, carboxylic acid, sulfonic acid, or phosphonic acid functional acrylates such as acrylic acid, hydroxy functional acrylates such as hydroxyethylacrylate, vinyl acetate and its hydrolyzed derivatives (e.g. polyvinylalcohol), acrylamides, polyethoxylated acrylates, and the like; hydrophilic modified celluloses, as well as polysaccharides such as starch and modified starches, dextran, and the like.

As discussed above, a hydrophilic silane or mixture of silanes may be applied to the surface of the fluid control film or impregnated into the article in order to adjust the properties of the fluid control film or article. Suitable silanes include the anionic silanes disclosed in U.S. Pat. No. 5,585,186 as well as non-ionic or cationic hydrophilic silanes. Cationic silanes may be preferred in certain situations and have the advantage that certain of these silanes are also believed to have antimicrobial properties.

As previously mentioned, the channels of fluid control films of the present invention can be of any geometry that provides desired liquid transport. In some embodiments, the fluid control film will have primary channels on only one major surface as shown in FIGS. 6a-6c and 6g, such as on first major surface 613 but not on second major surface 615, shown in FIG. 6a. In other embodiments, however, the fluid control film will have primary channels on both major surfaces, as shown in FIGS. 6i and 6j.

Figure 6A:
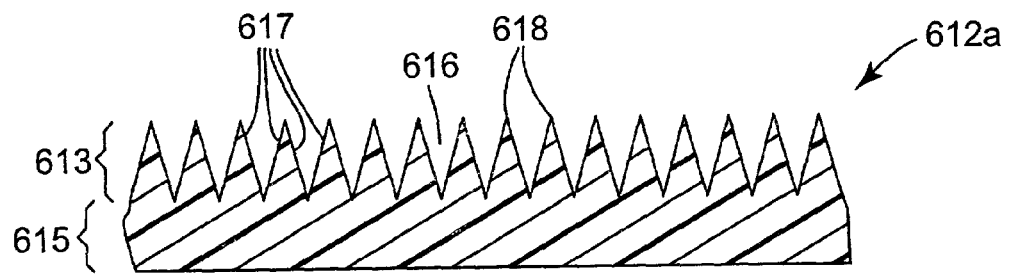
FIGS. 6a through 6j are cross-sectional cutaway views of illustrative embodiments of fluid control films of the present invention.

As shown in FIG. 6a, channels 616 can be defined within the layer 612a in accordance with the illustrated embodiment by a series of v-shaped sidewalls 617 and peaks 618. In some cases, the sidewalls 617 and peaks 618 may extend entirely from one edge of the layer 612 to another without alteration—although, in some applications, it may be desirable to shorten the sidewalls 617 and thus extend the peaks 618 only along a portion of the structured surface 613. That is, channels 616 that are defined between peaks 618 may extend entirely from one edge to another edge of the layer 612, or such channels 616 may only be defined to extend over a portion of the layer 612. Channels that extend only over a portion may begin at an edge of the layer 612, or they may begin and end intermediately within the structured surface 613 of the layer 612. The channels are defined in a predetermined, preferably ordered arrangement over a continuous surface of polymeric material.

Figure 6B:
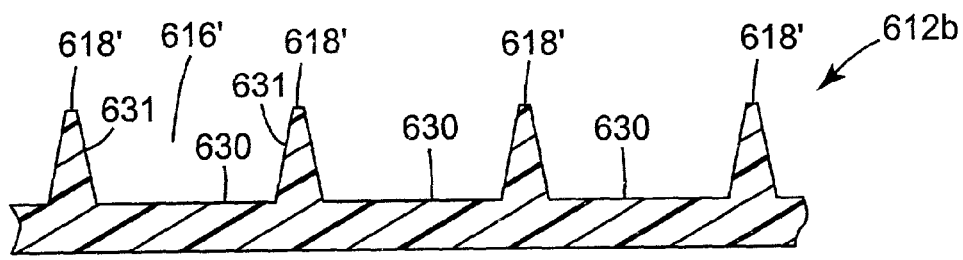

As shown in FIG. 6b, within layer 612b channels 616' have a wider flat valley between slightly flattened peaks 618'. Like the FIG. 6a embodiment, a cap layer can be secured along one or more of the peaks 618' to define discrete channels 616'. In this case, bottom surfaced 630 extend between channel sidewalls 631, whereas in the FIG. 6a embodiment, sidewalls 617 connect together along lines.

Figure 6C:
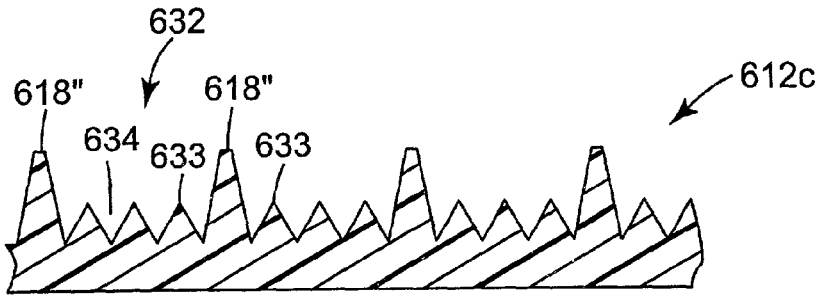

FIG. 6c illustrates a configuration where wide channels 632 are defined between peaks 618" in layer 612c, but instead of providing a flat surface between channel sidewalls, a plurality of smaller peaks 633 are located between the sidewalls of the peaks 618". These smaller peaks 633 thus define secondary channels 634 therebetween. Peaks 633 may or may not rise to the same level as peaks 618", and as illustrated create a first wide channel 632 including smaller channels 634 distributed therein. The peaks 618" and 633 need not be evenly distributed with respect to themselves or each other.

FIGS. 6d-6j illustrate various alternative embodiments of the fluid control film of the present invention. Although FIGS. 6a-6j illustrate elongated, linearly-configured channels, the channels may be provided in other configurations. For example, the channels could have varying cross-sectional widths along the channel length—that is, the channels could diverge and/or converge along the length of the channel. The channel sidewalls could also be contoured rather than being straight in the direction of extension of the channel, or in the channel height. Generally, any channel configuration that can provide at least multiple discrete channel portions that extend from a first point to a second point within the fluid transport device are contemplated. The channels may be configured to remain discrete along their whole length if desired.

Figure 6G:
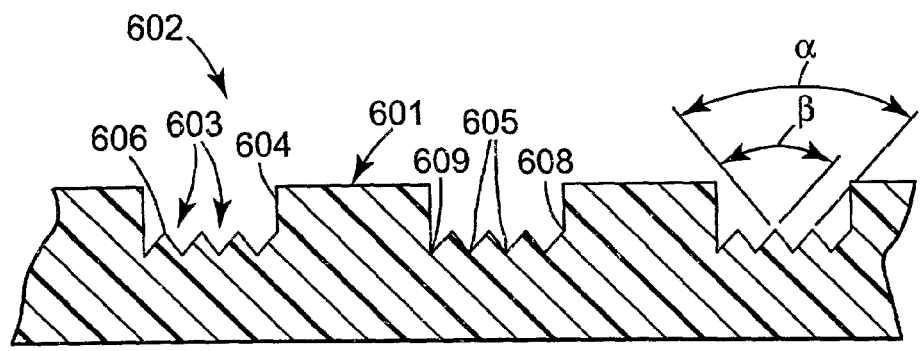
Figure 6D:
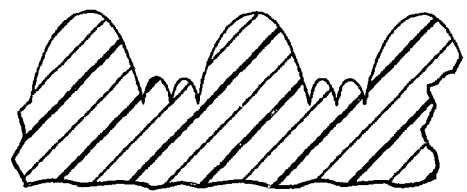
Figure 6E:
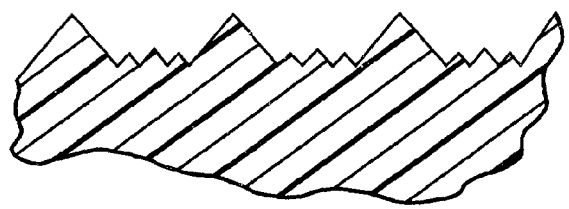
Figure 6F:
Figure 6H:
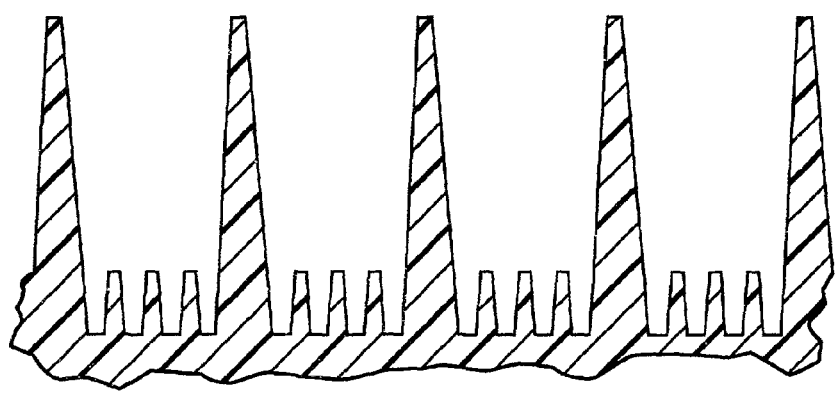
Figure 6I:
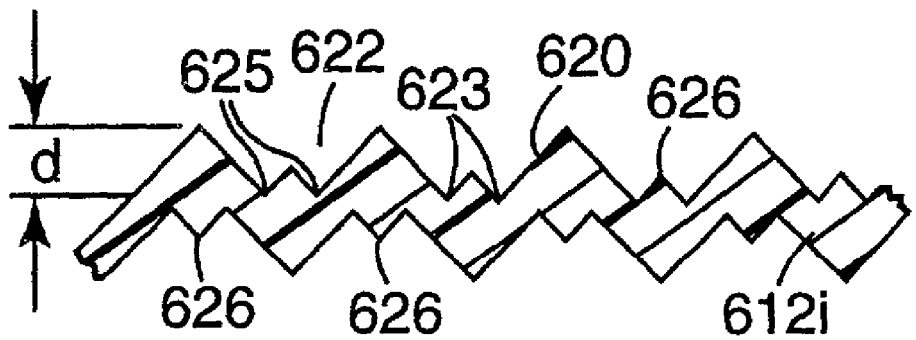
Figure 6J:
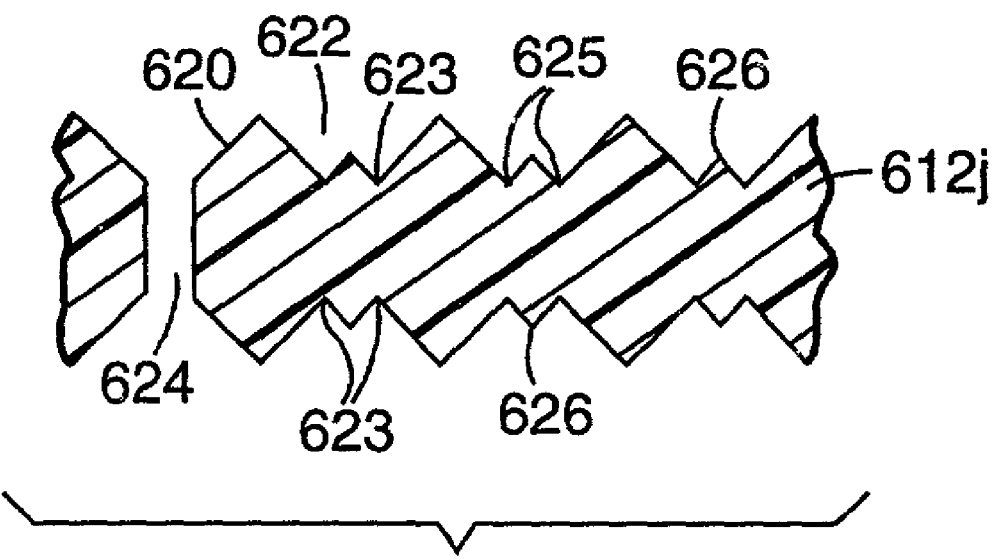

With reference to FIG. 6g, one preferred geometry is a rectilinear primary channel 602 in a flat film 601. The primary channel 602 has included secondary channels 603 which forms a multitude of notches 605. The notches 605 (or secondary channels 603, where the channels are V-shaped and have substantially straight sidewalls) have an included angle of (i.e., angle Alpha) from about 10° to about 120°, preferably from about 10° to about 100°, and most preferably from about 20° to about 95°. The notch included angle is generally the secant angle taken from the notch to a point 2 to 1000 microns from the notch on the sidewalls forming the notch, preferably the included angle is the secant angle taken at a point halfway up the secondary channel sidewalls. It has been observed that notches with narrower included angular widths generally provide greater vertical wicking distance. However, if Alpha is too narrow, the flow rate will become significantly lower. If Alpha is too wide, the notch or secondary channel may fail to provide desired wicking action. As Alpha gets narrower, the contact angle of the liquid need not be as low, to get similar liquid transport, as the contact angle must be for notches or channels with higher angular widths.

The primary channel included angle is not critical except in that it should not be so wide that the primary channel is ineffective in channeling liquid. Generally, the primary channel maximum width is less than 3000 microns and preferably less than 1500 microns. The included angle of a V-channel shaped primary channel will generally be from about 10 degrees to 120 degrees, preferably 30 to 90 degrees. If the included angle of the primary channel is too narrow, the primary channel may not have sufficient width at its base so that it is capable of accommodating an adequate number of secondary channels. Generally, it is preferred that the included angle of the primary channel be greater than the included angle of the secondary channels so as to accommodate the two or more secondary channels at the base of the primary channel. Generally, the secondary channels have an included angle at least 20 percent smaller than the included angle of the primary channel (for V-shaped primary channels).

With reference to FIGS. 6g and 6i, the depth of the primary channels (602, 622) (the height of the peaks or tops above the lowermost channel notch), "d", is substantially uniform, and is suitably from about 5 to about 3000 microns, typically from about 50 to about 3000 microns, preferably from about 75 to about 1500 microns, and most preferably is from about 100 to about 1000 microns. It will be understood that in some embodiments films with channels (602, 622) having depths larger than the indicated ranges may be used. If the channels are unduly deep, the overall thickness of the fluid control film will be unnecessarily high and the film may tend to be stiffer than is desired. The width of the primary channel at its base may be sufficient to accommodate two or more secondary channels.

FIGS. 6i and 6j illustrate fluid control films having primary channels on both major surfaces. As shown in FIG. 6i, the primary channels 622 within layer 612i may be laterally offset from one surface to the other surface or may be aligned directly opposite each other as shown in FIG. 6j. A fluid control film with offset channels as shown in FIG. 6i provides a maximum amount of surface area for wicking while at the same time using a minimum amount of material. In addition, a fluid control film with offset channels can be made so as to feel softer, due to the reduced thickness and boardiness of the sheet, than a fluid control film with aligned channels as shown in FIG. 6j. As shown in FIG. 6j, fluid control films 612j of the invention may have one or more holes or apertures 624 therein, which enable a portion of the liquid in contact with the front surface of the fluid control film to be transported to the back surface of the film, to improve liquid control. The apertures need not be aligned with the notch of a channel and do not need to be of about equal width as the channels. The surfaces of the fluid control film within the apertures is preferably hydrophilic.

As illustrated in FIGS. 6g and 6i, in each primary channel (602, 622) between sidewalls (604, 620) are at least two secondary channels (603, 623) and at least two notches (605, 625), the notch (605, 625) or notches of each secondary channel (603, 623) is separated by a secondary peak (606, 626). Generally, each secondary channel will generally have only one notch, but a secondary channel will have two notches if the secondary channel is rectangular. The secondary peak (606, 626) for V-channel shaped secondary channels is generally characterized by an included angle β which is generally equal to $(\alpha^1+\alpha^2)/2$ where $\alpha^1$ and $\alpha^2$ are the included angles of the two adjacent V-channel shaped secondary channels (603, 623), assuming that the two sidewalls forming each secondary channel are symmetrical and not curved. Generally, the angle β would be from about 10° to about 120°, preferably from about 10° to about 90°, and most preferably from about 20° to about 60°. The secondary peak could also be flat (in which case the included angle would theoretically be 0°) or even curved, e.g., convex or concave, with no distinct top or included angle. Preferably, there are at least three secondary channels (603, 623) and/or at least three notches for each primary channel (602, 622), included any notches (605, 625) associated with the end channels (notches 608 or 609) is shown in FIG. 6g.

The depth of one of the secondary channels (603, 623) (the height of the top of the secondary peaks 606 over the notches 605) is uniform over the length of the fluid control films, and is typically at least 5 microns. The depth of the secondary channels (603, 623) is generally 0.5 to 80 percent of the depth of the primary channels, preferably 5 to 50 percent. The spacing of the notches (605, 625) on either side of a peak 6 is also preferably uniform over the length of the fluid control film. Preferably the primary and/or secondary channel depth and width varies by less than 20 percent, preferably less than 10 percent for each channel over a given length of the fluid control film. Variation in the secondary channel depth and shape above this range has a substantial adverse impact on the rate and uniformity of liquid transport along the fluid control film. Generally the primary and secondary channels are continuous and undisturbed.

Certain articles of the present invention comprise fluid control film components that comprise layers of two or more films. These components are particularly suitable for active fluid transport.

Figure 7A:
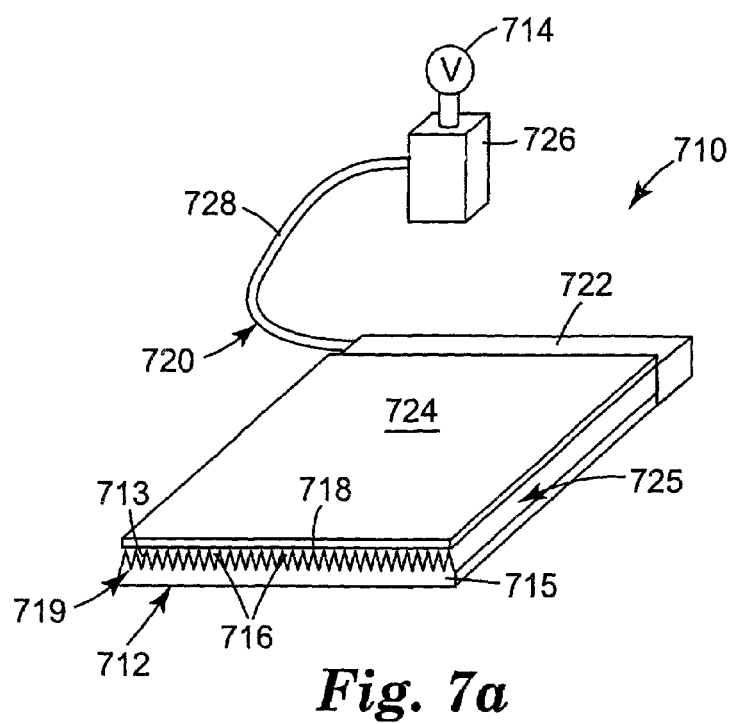
FIG. 7a is a perspective view of an active fluid transport device in accordance with the present invention having a structured layer combined with a cap layer to provide multiple discrete channels that are in communication with a vacuum source.

In FIG. 7a an active fluid transport device 710 is illustrated that includes a layer 712 of polymeric material that has a structured surface 713 on one of its two major surfaces. The device 710 also includes a source 714 for providing a potential to assist in moving a fluid over the structured surface 713 of the active fluid transport device 710. Layer 712 also includes a body layer 715 from which the structured surface 713 projects. Body layer 715 serves to support structured surface 713 to retain the individual structured features together in layer 712.

Layer 712 may be comprised of flexible, semi-rigid, or rigid material, which may be chosen depending on the particular application of the active fluid transport device 710. The layer 712 comprises a polymeric material because such materials can be accurately formed to create a microstructured surface 713. Substantial versatility is available because polymeric materials possess many different properties suitable for various needs. Polymeric materials may be chosen, for example, based on flexibility, rigidity, permeability, etc. The use of a polymeric layer 712 also allows a structured surface to be consistently manufactured to produce a large number of and high density of channels that when capped form discrete fluid flow channels 716. Thus, a highly distributed fluid transport system can be provided that is amenable to being manufactured at a high level of accuracy and economy. The structured polymeric surface 713 may be made from the same or different materials of the body layer 715.

As shown in FIG. 7a, each of the channels 716 is opened at one edge of the layer 712 to define channel inlets 719. Fluid can thus pass through the inlets 719 guided by the channels 716 toward a further edge of the layer 712 to a connector 720. The connector 720 preferably is in fluid communication with each of the channels 716 through outlets (not shown) and also is in fluid communication with the potential source 714. The connector 720 may be fashioned in a variety of forms but as illustrated in FIG. 7a, it includes a manifold 722. Manifold 722 is provided with a plenum (not shown) that is defined internally therein and which is in fluid communication with channels 716. The plenum may simply comprise a chamber within the manifold 722 that is sealingly connected to at least a plurality of the channels 716. The manifold 722 may be flexible, semi-rigid, or rigid, like the layer 712. A second manifold (not shown) also may be provided at the side of layer 712 having inlets 720 so as to supply fluid to the channel 716, depending on the particular application. The manifold may be formed using microreplicated channels (e.g., converging channels).

In accordance with the invention, the connector may take on essentially any adaptation that enables the potential to be transferred from the source to the multiple channels. Although a manifold with a plenum and a tubing have been described, other connectors—such as compression couplings, or seals and gaskets that fluidically join a conduit to the flow channels and permit the isolation or partition of regions of higher and lower potential from the surrounding environment—are contemplated for use in this invention. The connector could also include capillary fibers, for example, less than 10 μm in inner diameter, each in fluid communication with an individual channel to allow individual fluids to flow discretely through separate channels. The connector could also be a molded chamber(s), a microstructured fluid conduit integrally or nonintegrally disposed relative to the discrete flow channels, or for example, a system or mechanism that allows the discrete microstructured flow channels to be seated in a centrifuge or that allows a flow stream such as a jet to be directed at channel inlets or outlets.

To close off or enclose at least part of the channels 716 at the peaks 718, a cap layer 724 may be juxtaposed against the structured surface. Cap layer 724 thus closes at least a plurality of the channels to create discrete flow channels 716 in a capillary module 725. The capillary module typically would have a thickness of 1 to 10 millimeters (mm), more typically 2 to 6 mm. Cap layer 724 may likewise sealingly connect to the manifold 722 so that plural discrete channels 716 provide active fluid transport channels based upon the creation of a potential difference across the channels 716 from a first potential to a second potential. Cap layer 724 typically has a thickness of about 0.01 to 1 mm, more typically 0.02 to 0.5 mm. If the channels of the invention are hermetically sealed then the flexible system of channels could generally withstand high pressure without rupture, as a result of the hoop strength of the small individual channels.

The cap layer 724 may be bonded to the peaks 718 of some or all of the structured surface 713 to enhance creation of discrete channels 716. This can be done thermally or by using conventional adhesives that are compatible with the cap layer material 724 and the polymeric structured layer 712. Formation of discrete channels 716 may be accomplished through heat bonding, ultrasonic welding, compression, or mechanical engagement such as an interference fit. Bonds may be provided entirely along the peaks 718 to the cap layer 720, or the bonds may be spot welds or bonds that may be placed thereon in an ordered or random pattern.

Cap layer 724 preferably is made from a polymeric material such as the polymers described below for the structured polymeric layer. Optionally, cap layer 724 may be a material such as a spunlaced, spunbond, blown microfiber or carded nonwoven. Polymers may be chosen such that the cap layer can be secured to the structured surface 713 without using an adhesive. Such a polymer could be chosen such that the cap layer becomes securely welded to the structured surface by applying heat, for example, as from an ultrasonic welding operation.

The potential source may comprise essentially any means capable of establishing a potential difference along a plurality of the flow channels 716 to encourage fluid movement from a first location to a second location. The potential is sufficient to cause, or assist in causing, fluid flow through a plurality of flow channels 716, which is based in part on the fluid characteristics of any particular application. As shown in FIG. 7a, the potential source 714 may comprise a vacuum generator (V) that is conventionally or otherwise connected to an optional collector receptacle 726. The collector receptacle 726 is fluidically connected to the manifold 722 by way of a conventional flexible tube 728. Thus, fluid can be drawn from outside the capillary module 725 into the inlets 719, through channels 716, through manifold 722, through tube 728, and into the collection receptacle 726. The receptacle 726 may advantageously be openable to empty its contents or may be otherwise connected to conventional drainage systems.

In the case where the potential source 714 comprises a vacuum generator (V), the vacuum provided to the channels 716 via manifold 722 can be sufficient to adequately seal the cap layer 724 to the peaks 718. That is, the vacuum itself will hold the cap layer 724 against peaks 718 to form discrete channels 716. Preferably, each of the channels 716 that are defined by the structured surface 713 is closed off by the cap layer 724 so as to define a maximum number of discrete channels 716 capable of independently accommodating the potential. Fluid crossover between channels 716 may be effectively minimized, and the potential provided from an external source can be more effectively and efficiently distributed over the structured surface 713 of layer 712. When the potential source 714 comprises a vacuum generator, manifold 722 need not be sealed to channels 716 but may be simply placed adjacent an open section of channels 716.

Connection between a microstructure-bearing surface, or capillary module, to a fluid conveyance or potential source can be achieved through a detachable or affixed manifold or manifolds as required. Multiple potential sources may also be employed depending on the particular adaptation or application. Pressure differential is an efficient fluid motivation method or potential that may be used to drive flow across the microstructure-bearing surface(s). Pressure differential can be established readily through use of a pumping system and applied either in the form of positive or negative pressure.

Other potential sources 714 may be used in the present invention instead of or in conjunction with a vacuum generation device (V). Essentially any manner of causing or encouraging fluid flow through the channels 716, particularly liquid flow, is contemplated for using this invention. The potential source is separate from the channeled structure and/or capillary module, or in other words is not intrinsic to the channeled structure and/or capillary module. That is, the invention does not rely solely on the properties of the channeled structure to cause fluid movement, for example, by capillary action. Examples of other potential sources include but are not limited to, vacuum pumps, vacuum aspirators, pressure pumps and pressure systems such as a fan, magneto hydrodynamic drives, acoustic flow systems, centrifugal spinning, hydrostatic heads, gravity, absorbents, and any other known or later developed fluid drive system utilizing the creation of a potential difference that causes or encourages fluid flow to at least some degree. Additionally, any applied field force that acts directly on the fluid such as a centrifugal force or magnetic field that causes fluid to move within the channels of the invention may be considered a fluid motive potential. Fluid may also be caused to flow through channels by the action of a siphon where atmospheric pressure creates the potential to move fluid in the channels.

Although the fluid transport device shown in FIG. 7a has a structured surface comprising multiple v-shaped peaks 718 (e.g., as shown in FIG. 6a), other configurations are contemplated.

Figure 7B:
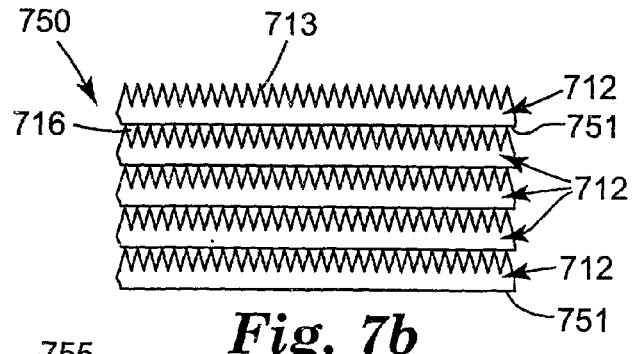
FIG. 7b is an end view of a stack of structured layers that are disposed upon one another so that bottom major surfaces of the layers close off the structured surface of a lower layer to define multiple discrete channels.

As shown in FIG. 7b, a plurality of layers 712, each having a microstructured surface 713 can be constructed to form a stack 750. This construction clearly multiplies the ability of the structure to transport fluid because each layer significantly increases flow capacity. The layers may comprise different channel configurations and/or number of channels, depending on a particular application. Furthermore, this type of stacked construction can be particularly suitable for applications that are restricted in width and therefore require a relatively narrow fluid transport device from which a certain fluid transfer capacity is desired. Thus, a narrow device can be made having increased flow capacity.

A significant advantage of the stack 750 is that a second major surface 751 of layers 712 (the surface facing opposite the structured surface 713) can close off or cap the channels of an adjacent layer 712. In other words, separate cap layers are not required, although they may be utilized, particularly to cover the exposed microstructured surface 713 of the uppermost layer. Separate cap layers, however, could be disposed over the second major surface 751 as an additional layer. The material chosen for such an additional layer could be a polymeric material or otherwise depending on the particular application. The layers in the stack may be bonded to one another in any number of conventional ways as described above, or they may simply be stacked upon one another such that the structural integrity of the stack can adequately define discrete flow channels. This ability may be enhanced, as described above, when a vacuum is utilized as the potential source. The second major surface 751 may be planar as shown, or it may be a structured surface similar to or different from surface 713.

Although the device shown in FIG. 7b includes a stack of 5 structured surfaces 712, stacks may be configured that have other numbers of stacks, for example, greater than 10 or even greater that 100 structured layers, and may include tributary stacks that converge into a larger stack. For example, the five-layered stack shown in FIG. 7b could be divided into quarters, and each of the four tributary stacks (which possess channel inlets) could converge into the larger stacked configuration as shown in FIG. 7b which in turn could be attached to a connector that communicates with a potential source. The stack could include multiple connectors to allow multiple potential sources of varying potential to be attached to as subsets in the stack.

Figure 7C:
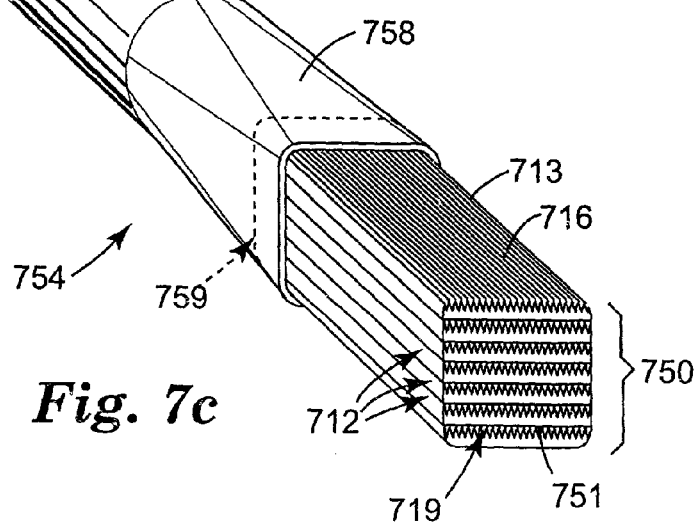
FIG. 7c is a perspective view of an aspirator in accordance with the present invention utilizing a stack of multiple microstructured layers.

In FIG. 7c, a stacked construction, such as shown in FIG. 7b, is used in an aspirator 754. The aspirator 754 employs a stack 750 that comprises a plurality of layers 712, each having a microstructured polymeric surface 713 over one major surface thereof. The second major surface 751 of layers 712 acts as a cap layer, closing the channels 716 of the adjacent sub layer 712 to create a stack or capillary module 750 having a multiplicity of channel inlets 719 at the aspirator tip or end. The second major surface 751 may be polymeric, or it may be covered with other materials, e.g. metal foils, etc., as desired.

The capillary module 750 can be joined to a connector 755 that includes a tubing 756 and an adapter 758. The tubing 756 may be fastened or otherwise joined to a potential source, such as a vacuum. The adapter 758 joins the square cross-sectional capillary module 750 to the round cross-sectional tubing 756 at the sealing connection region 759. The adapter 758 may be conventionally, sealingly connected to tubing 756 and to the module 750 by adhesive or other bonding techniques. The stack or module 750 may or may not be further enclosed by a conduit or tubing. Alternatively, the tubing 756 and module 750 can be connected together by a section of shrinkable tubing into which ends of the tubing 756 and the module 750 are inserted before shrinking. For example, heat shrinkable tubing or pre-stretched elastomeric tubing may be used. The layers 712, and thus the stack 750, may extend only a short distance from the adapter 758 so as to provide a relatively stiff aspirator end, or the layers 712 may extend further to make the aspirator 754 more flexible. To provide a flexible and conformable aspirator end, the individual layers 712 preferably are not bonded or otherwise secured to each other over the whole surface of the layer, particularly at the end, to allow the layers 712 to slide or move relative to one another in the longitudinal direction of the channels 712. This independent sliding motion enables the tip to be bent around an axis normal to the flow channels 716. When used in an aspirator, the module typically would be about 1 to 10 cm in length. A stiff aspirator may be more applicable for insertion into tight spaces, while flexibility may be desired so that the aspirator tip can be positioned at a more distal location while conforming to a path to that location.

A sheath could also be applied over the capillary module 750 as described. Dependent on the application, a porous or closed sheath could be placed around the stack. A porous sheath could be used for applications where the sheath acts as a sieve or filter, and a closed sheath construction might be particularly suited to applications in endoscopic surgical procedures where liquid fluid delivery or extraction is needed.

The layers 712 may be assembled so that they are not adhered to one another, although they may connected as such if needed. Where the layers 712 are not bonded together, the integrity of the stack 750, and/or a vacuum applied through tubing 756 can be relied upon to adequately define independent flow channels 716. In accordance with the present invention, the microstructured surface 713 of the layers 712 define flow channels 716 that promote single-phase liquid flow. This is again advantageous in that noise is reduced, which is particularly beneficial in the medical field.

Another advantage of the aspirator 754, which comprises a stack of individual layers 712 that are unattached to one another, is that the stack 750 may be divided and even further subdivided into a plurality of aspirator branches. That is, a part of the stack 750 may be directed to one particular location where a fluid is to be extracted, while another portion of the stack 750 is directed to another area where additional fluid is extracted. Particularly, where the aspirator 754 relies on a vacuum supplied through conduit or tubing 756 to remove fluid, any number of such divisions can be made whereby a plurality of individual discrete flow channels are provided within each branch. Tubing 756 could also be subdivided so that fluid from each particular branch or subdivision in stack 750 is directed to its own respective conduit to allow appropriate fluid flow. Simultaneous irrigation and/or aspiration could be achieved by such a device. That is, the separate conduits could be adopted to transport an irrigation fluid and an aspirated fluid. This feature may be particularly beneficial for medical uses, including dental uses, for aspirating more than one spot at a time.

A stacked module construction may include plural stacks arranged next to one another. That is, a stack such as shown in FIG. 7b may be arranged adjacent to a similar or different stack. Then, they can be collected together by an adapter, such as shown in FIG. 7c, or they may be individually attached to a fluid transfer tubing or the like.

Although the aspirator shown in FIG. 7c has essentially a linear profile, it may be desirable in some embodiments to use an aspirator that has a different configuration. For example, the tubing 756 or the adapter 758 and/or the stack 750 may be curved or curvable to allow the aspirator to reach difficult areas or to allow the aspirator to support itself. For example, if the aspirator shown in FIG. 7c could be used by a dentist to withdraw saliva and aqueous rinsing fluids that are present in the patient's mouth. If the aspirator was hooked at its end, it could rest on the patient's lip. The tubing 756 or adaptor 758 desirably is flexible to achieve such a curved configuration and may be made of a dead soft material, or may contain such a material, to enable the aspirator to be temporarily bent into and retain such a curved configuration. Such a device would be highly beneficial in that the dentist could more easily communicate with the patient and vice versa without having to overcome the noise that is associated with conventional dental aspirators.

Other features or items may also be provided in front of the inlets 719 to the channels 716 for added functions. For example, a soft fibrous end may be placed on the aspirator tip by adhering a mass of cotton gauze or sponge-like material. This feature may be particularly useful for dental or other medical applications. Features could also be added on the channel outlet side of the module to provide, for example, an irrigation function in conjunction with or in lieu of an aspirator.

Current aspirator technologies generally utilize relatively larger diameter tubes to acquire and convey the aspirated liquid. It is not uncommon for these tubes to have an inner diameter of one centimeter or larger. Unless the tubes are completely flooded during use, which is not typical, the aspirator functions primarily in two-phase flow with air being the continuous phase that motivates the liquid movement in the flow system. This requires a relatively large air-to-liquid ratio, one in which the momentum of the flowing air is sufficient to carry the liquid. The required momentum of the air flow has many negative effects on the function of typical medical aspirators. These negative effects may include trauma to tissues contacted at the aspirator tip, high volumetric air flows that can cause atomization of potential biohazardous liquids, increasing occupational exposure, and the general noise level of their operation.

Figure 9A:
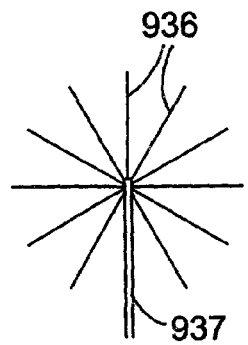
FIGS. 9a and 9b are top schematic views of structured layers illustrating alternative channel structures that may be used in a device in accordance with the present invention.
Figure 9B:
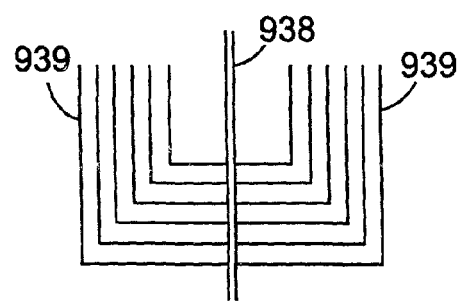

FIGS. 9a and 9b schematically illustrate channel configurations in plan view that may define a structured surface in a fluid transport device of the invention. As shown, multiple discrete non-parallel converging channels 936 provide for intermediate collection of fluid. These converging channels 936 connect to a single discrete channel 937. This minimizes the provision of outlet ports to one. As shown in FIG. 9b, a central channel 938 connects to a plurality of channel branches 939 that may be designed to cover a particular area for similar reasons. Again, generally any pattern is contemplated in accordance with the present invention as long as a plurality of discrete channels is provided over a portion of the structured surface from a first point to a second point. Like the above embodiments, the patterned channels shown in FIGS. 9a and 9b are preferably covered with a cap layer for further defining discrete flow channels that allow the potential to be accommodated along a particular channel essentially independent of its neighboring channels.

As to any of the channels contemplated above and in accordance with the present invention, such channels are defined within a structured layer by the structured surface of a first major surface of the layer. The channels in accordance with the present invention are configured to be discrete to allow any one channel to receive fluid from the ambient environment independently of the other channels. The microstructured size of each channel encourages single-phase flow of fluid in bulk volumes. Without having air entrained in the liquid, noise generation is significantly reduced and less stress can be placed on liquids that are transported through the active fluid transport device.

The individual flow channels of the microstructured surfaces of the invention are substantially discrete. That is, fluid can move through the channels independent of fluid in adjacent channels. The channels independently accommodate the potential relative to one another to direct a fluid along or through a particular channel independent of adjacent channels. Preferably, fluid that enters one flow channel does not, to any significant degree, enter an adjacent channel, although there may be some diffusion between adjacent channels. It is important to effectively maintain the discreteness of the micro-channels in order to effectively transport the fluid and maintain advantages that such channels provide. Not all of the channels, however, may need to be discrete for all embodiments. Some channels may be discrete while others are not. Additionally, channel "discreteness" may be a temporary phenomenon driven, for example, by fluctuating pressures.

The structured surface is a microstructured surface that defines discrete flow channels that have a minimum aspect ratio (length/hydraulic radius) of 10:1, in some embodiments exceeding approximately 100:1, and in other embodiments at least about 1000:1. At the top end, the aspect ratio could be indefinitely high but generally would be less than about 1,000,000:1. The hydraulic radius of a channel is no greater than about 300 micrometers. In many embodiments, it can be less than 100 micrometers, and may be less than 10 micrometers. Although smaller is generally better for many applications (and the hydraulic radius could be submicron in size), the hydraulic radius typically would not be less than 1 micrometers for most embodiments. As more fully described below, channels defined within these parameters can provide efficient bulk fluid transport through an active fluid transport device.

The structured surface can also be provided with a very low profile. Thus, active fluid transport devices are contemplated where the structured polymeric layer has a thickness of less than 5000 micrometers, and possibly less than 1500 micrometers. To do this, the channels may be defined by peaks that have a height of approximately 5 to 1200 micrometers and that have a peak distance of about 10 to 2000 micrometers.

Microstructured surfaces in accordance with the present invention provide flow systems in which the volume of the system is highly distributed. That is, the fluid volume that passes through such flow systems is distributed over a large area. Microstructure channel density from about 10 per lineal cm and up to 1,000 per lineal cm (measured across the channels) provides for high fluid transport rates. Generally, when a common manifold is employed, each individual channel has an aspect ratio that is at least 400 percent greater, and more preferably is at least 900 percent greater than a manifold that is disposed at the channel inlets and outlets. This significant increase in aspect ratio distributes the potential's effect to contribute to the noted benefits of the invention.

Suitable fluid channels for use in the present invention may be of any suitable geometry but are generally rectangular (typically having depths of 50 μm to 3000 μm and widths of 50 μm to 3000 μm or "V" channel patterns (typically having depths of about 50 μm to 3000 μm and heights of 50 μm to 3000 μm) with an included angle of generally 20 to 120 degrees and preferably about 45 degrees. The presently preferred structure has a nested construction wherein the master channels are 200 μm deep and repeat every 225 μm with three equally spaced channels in the base each 40 μm deep. Compound channels are also possible and often preferably such as rectangular channels that contain smaller rectangular or V channels within.

As mentioned previously, suitable fluid control film components of the present invention may be made through a process such as extrusion, injection molding, embossing, hot stamping, etc. In one technique, a substrate (e.g., a thermoplastic material) is deformed or molded. This process is usually performed at an elevated temperature and perhaps under pressure. The substrate or material is preferably made to replicate or approximately replicate the surface structure of a master tool. Since this process produces relatively small structures and is sometimes repeated many times over the process is referred to as microreplication. Suitable processes for microreplication are described in U.S. Pat. No. 5,514,120.

In one embodiment, the present invention relates to wound dressings that incorporate fluid control film (e.g., microreplicated wicks) to move fluid from one area and transfer it to another, e.g., by capillary action. The presence of the fluid control film allows for a dressing that can rapidly handle (e.g., absorb) large amounts of wound exudate while also optionally allowing visual observation of the wound. The fluid control film component of the present invention may serve to move fluid such as wound exudate away from the wound to an absorbent, to supply a fluid such as a medicament to a wound, or both.

Exemplary wound dressings of this invention are described and illustrate certain features of the present invention. In a preferred embodiment the wound dressing includes: (i) a fluid control film as previously discussed; (ii) an optional absorbent material; (iii) an optional backing layer; and (iv) an optional adhesive. Each of these components is discussed in detail herein. The present invention also provides assemblies of a dressing and a separate fluid control film component.

An optional absorbent may be used in articles of the present invention, e.g., to serve as a reservoir to collect fluid moved off or away from the wound site. Preferably the absorbent is capable of absorbing fluid relatively quickly. More preferably, the absorbent is capable of releasing the fluid (e.g., through evaporation through the dressing). The articles of this invention have the advantage of allowing a wide variety of product designs. Preferred designs can incorporate increased surface area of the absorbent material, thereby allowing for management of more highly exuding wounds.

Suitable absorbent materials include fibrous textile type materials, including woven, non-woven, knit, and stitch bonded materials or absorbent foams. Alternatively, the absorbent can comprise an absorbent polymer such as a hydrocolloid or hydrophilic polymer such as a supersorber. The hydrocolloid (e.g. starch, modified cellulose, gelatin or other protein, polysaccharide, etc) or supersorber (e.g. modified starch, acrylates, starch/acrylate copolymers, acrylamides and other vinyl polymers, etc) may be immobilized in a matrix such as a hydrophobic matrix of conventional hydrocolloid dressings or may alternatively be part of a hydrophilic gel matrix (e.g. a UV or E-beam cured acrylate). The absorbent may also comprise both a fibrous textile and an absorbent polymer. The absorbent pad may optionally contain an antimicrobial agent.

Preferred dressings keep the absorbent pad off of the skin, thereby preventing damage to healthy tissue. This may be accomplished using porous films, for example, such as MICRODON, VISPORE, etc., which may be placed between the skin and the absorbent.

If desired, the dressing may be constructed using a two-piece fastener system such as those disclosed in U.S. Ser. No. 09/235,925.

Suitable backings for use in wound dressing articles of the present invention include conventional backings known in the art including non-woven and woven fibrous webs, knits, films, foams and other familiar backing materials. Preferred backings include thin (e.g. less than about 1.25 mm and preferably less than about 0.05 mm) and elastomeric backings. These types of backings help ensure conformability and high adhesion around the wound site. Preferred backing materials include polyurethanes (e.g., ESTANE), polyether polyesters (e.g., HYTREL), polyether amides (e.g., PEBAX) as well as polyolefins e.g., ENGAGE). The backings also preferably provide a high moisture vapor transmission rate (MVTR) either through the film itself or by using microscopic pores or perforations in the film. In the latter case, a suitable medical adhesive preferably covers the entire backing to ensure that the backing does not allow influx of microbial contamination. When thin film backings are used wrinkle free application can be difficult. Any delivery method known to the art may be employed, including those of U.S. Pat. Nos. 4,485,809, 4,600,001, and RE 33,727, as well as EPO No. 0 051 935. The preferred method is a carrier delivery such as that disclosed in U.S. Pat. No. 5,738,642. In this embodiment, the backing is supported by a removable heat sealed carrier attached to the top face of the backing.

The carrier material used to supply the carriers for dressings manufactured according to the present invention is preferably substantially more rigid than the backing to prevent the backing from wrinkling during application. The carrier material must also be heat-sealable to the backing, with or without the low adhesion coating described below, for the purpose of manufacturing the preferred dressings. In general, the preferred carrier materials can include, but are not limited to, polyethylene/vinyl acetate copolymer-coated papers and polyester films. One example of a preferred carrier material is a polyethylene/vinyl acetate copolymer-coated super calendared Kraft paper (1-90BKG-157 PE; Daubert Chemical Co.).

Suitable adhesive for use in wound dressing articles of the present invention include any adhesive that provides acceptable adhesion to skin and is acceptable for use on skin (e.g., the adhesive should preferably be non-irritating and non-sensitizing). Preferred adhesives are pressure sensitive and in certain embodiments preferably have a relatively high moisture vapor transmission rate to allow for moisture evaporation. Suitable pressure sensitive adhesives include those based on acrylates, polyurethanes, KRATON and other block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components such as an antimicrobial agent. It is anticipated that removable liners may be used to protect the adhesive surface prior to use. In addition, conventional frame components may be used if desired, e.g., to keep the dressing from wrinkling prior to application to the patient.

The preferred pressure sensitive adhesives that can be used in the adhesive composites of the present invention are the normal adhesives that are applied to the skin such as the acrylate copolymers described in U.S. Pat. No. RE 24,906, particularly a 97:3 iso-octyl acrylate:acrylamide copolymer. Also preferred is an 70:15:15 isooctyl acrylate-ethyleneoxide acrylate:acrylic acid terpolymer, as described in U.S. Pat. No. 4,737,410 (Example 31). Other useful adhesives are described in U.S. Pat. Nos. 3,389,827, 4,112,213, 4,310,509 and 4,323,557. Inclusion of medicaments or antimicrobial agents in the adhesive is also contemplated, as described in U.S. Pat. Nos. 4,310,509 and 4,323,557.

Liners which are suitable for use in the adhesive composites of the present invention can be made of kraft papers, polyethylene, polypropylene, polyester or composites of any of these materials. The liners are preferably coated with release agents such as fluorochemicals or silicones. For example, U.S. Pat. No. 4,472,480 describes low surface energy perfluorochemical liners. The preferred liners are papers, polyolefin films, or polyester films coated with silicone release materials. Examples of commercially available silicone coated release papers are POLYSLIK™ silicone release papers available from James River Co., H.P. Smith Division (Bedford Park, Ill.) and silicone release papers supplied by Daubert Chemical Co. (Dixon, Ill.). The most preferred liner is 1-60BKG-157 paper liner available from Daubert, which is a super calendared Kraft paper with a water-based silicone release surface.

Suitable fluid control film containing wound dressings are designed to utilize micro-grooves or channels (e.g., produced by microreplication) to transport fluid, e.g., by capillary action. Preferred designs may also incorporate pores or openings in the film to allow movement of fluid through the fluid control film, e.g., to the other side of the film and/or to an optional absorbent. One preferred dressing incorporates a fluid control film as a fluid wick that may be incorporated into the dressing by heat sealing or using adhesives into preferred shapes and designs. Alternatively, the fluid wick can be part of the backing layer itself or may be provided as a structured adhesive.

The dressings of the present invention may take on a variety of forms. In one embodiment a preferred feature is that the dressing moves fluid from one portion of the dressing to an absorbent due to capillary channels. Preferred dressings also keep the absorbent pad off of healthy tissue and allow for the dressing to have a high MVTR (at least in one section).

In order to function to remove wound exudate it is a preferred feature that the fluid control film be in communication with both the fluid source (e.g. the wound) and the absorbent. Typically the fluid control film will be placed directly above the wound site and transport fluid to the absorbent section of the dressing. The fluid control film of the present invention may transport fluid in any direction suitable to move fluid between the wound site and a remote site on the dressing. For example, this may be along the length of a dressing (illustrated in FIGS. 1a and 1b), the width of the dressing, may be radially patterned (FIG. 1c), or may incorporate combinations of these flow patterns.

Medicaments may be incorporated into articles of the present invention. Suitable medicaments include antimicrobials, antibiotics, analgesics, healing factors such as vitamins, growth factors, nutrients and the like, or any combination of any of the foregoing, as well as simple flushing with isotonic saline solutions. In preferred embodiments the wound dressings may serve both functions of delivering and removing fluid from the wound site.

Figure 1B:
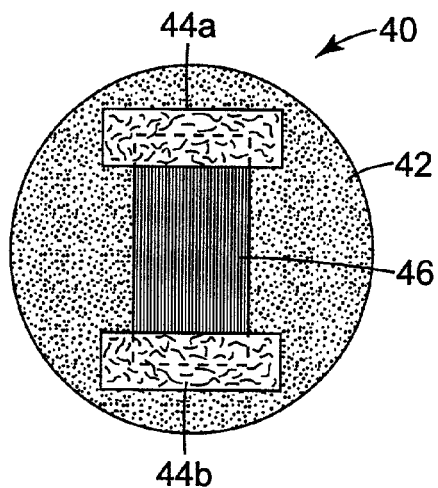
Figure 1C:
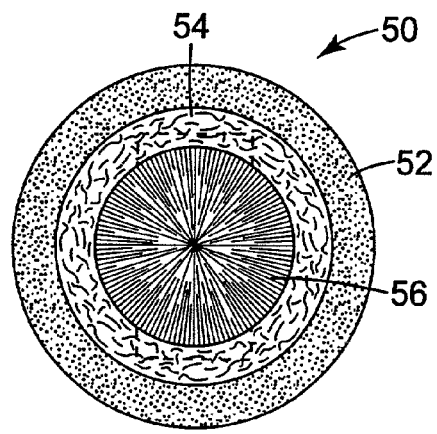
Figure 1F:
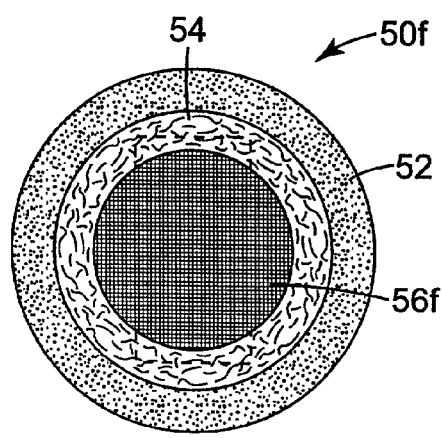

FIG. 1a illustrates one embodiment of a wound dressing 30 of the present invention. Dressing 30 comprises film backing 32 with adhesive surface; absorbent ring 34; and fluid control film 36. The channels in the fluid control film 36 transport fluid from a covered wound site to the absorbent ring 34. Alternatively, as shown in FIG. 1b two pieces of absorbent material (44a and 44b) may be utilized in place of absorbent ring 34 of FIG. 1a. As shown in FIG. 1c, fluid control film 56 comprises a plurality of channels radially extending toward a periphery. Alternatively, as shown in FIG. 1f, fluid control film 56f comprises a plurality of channels in a cross-hatched pattern. In either case, absorbent ring 54 is positioned to absorb fluid transported via the fluid control film. Film backing 52 may be provided with an adhesive layer to facilitate attachment of the dressing to the patient. The dressings of the present invention may also incorporate fenestrations, slits, or other patterns to allow conformability to the patient or to facilitate use of a auxiliary medical device such as an IV tube or wound drain.

FIG. 1d is a bottom view of an alternative wound dressing 60 of the present invention. In this embodiment, fluid control film 66 is placed against a porous dressing 62 on the side away from the patient. Holes, pores, or perforations through backing 62 communicate fluid to the fluid control film surface. The fluid is thereby transported to absorbent material 64.

Wound dressing 20 of FIG. 1g is designed to provide a high MVTR. In this embodiment, an adhesive coated thin film 22 is supported on liner 26 and by carrier frame 24. The adhesive coated thin film 22 has at least one hole 27 extending through the adhesive and film. Preferably multiple holes are employed and are distributed across the wound surface. Sealed to the top side of thin film 22 (the side away from the skin) is a high MVTR fluid control film 28. Film 28 may be sealed to thin film 22 by any conventional means such as heat, ultrasonic welding, use of an adhesive, etc. Fluid control film 28 comprises microreplicated channels which serve to distribute excess wound exudate across film 28 to increase surface area for evaporation. The microreplicated pattern is also designed to prevent film 28 from bonding to film 22 as the wound exudate evaporates from the dressing. The dressing is applied by first removing liner 26 to expose the adhesive. Applying the dressing over the wound and subsequently removing carrier 24.

As stated previously the fluid control film structure (e.g., its microreplicated pattern) may be incorporated into the wound dressing as a separate component, or as an integral part of the dressing (e.g., in part or all of the film backing or into the adhesive layer of the dressing).

When the fluid control film is a separate piece it is usually present as a piece of film preferably produced either by a film extrusion or hot stamping process. It should be understood that this pattern may be made off-line or may be made integral with the converting operation. The film may be produced with one or both major surfaces having a microreplicated pattern.

It is preferred to maintain the MVTR of the dressing quite high to also allow for evaporation of the exudate. This feature can facilitate prolonged wearing of the dressing. One preferred method of achieving high MVTR is to incorporate thin dressings (e.g., at least a portion of its total area is thin).

The fluid control film may also be part of the backing itself. As with the film the microreplicated pattern may be manufactured into the backing off-line as part of an extrusion, embossing, or other process or it may be incorporated into the film as part of the converting process. The backing may incorporate the pattern on one or both surfaces as described above for the film. It is presently believed that the fluid control film structure is preferably incorporated into the film backing itself wherein the film contacts the wound fluid directly and transports the fluid to a remote absorbent. This design is preferred since it both provides a very high MVTR product and lower cost manufacturing since no additional fluid wick component is required. In this case where the film has the fluid control film capability it is understood that the adhesive layer may be discontinuous to allow fluid to enter the structure on the film backing. Preferably no adhesive is present on the film wick structure immediately above the wound site since this will provide for the most efficient fluid wick capability and the highest MVTR. If the adhesive layer is sufficiently hydrophilic and allows moisture passage rapidly, it may be a continuous layer such as is shown in FIG. 2h.

The fluid wick may also be incorporated into an adhesive layer. In this case the adhesive must either be supported by a microreplicated liner having the mirror image of the fluid wick pattern or the adhesive must have sufficient yield stress and/or creep resistance to prevent flow and loss of the pattern during storage. Increase in yield stress is most conveniently accomplished by slightly crosslinking the adhesive (e.g., using covalent and/or ionic crosslinks or by providing sufficient hydrogen bonding).

Figure 2A:
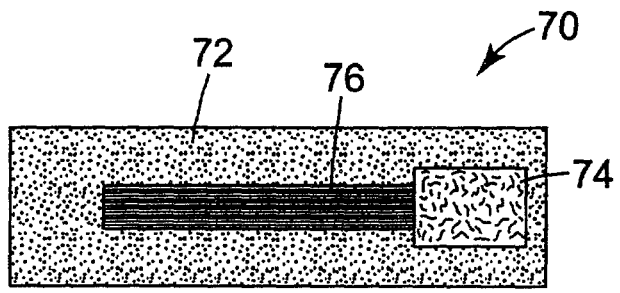
Figure 2B:
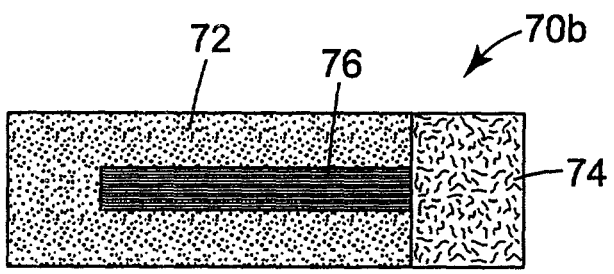

FIG. 2a illustrates a simple wound dressing 70 of the present invention having a film backing 72 with adhesive surface; absorbent pad 74 at one end of the dressing; and fluid control film 76. The channels in the fluid control film 76 transport fluid from a covered wound site to the absorbent 74. This design illustrates how dressings can be constructed where the absorbent pad is remote from the tissue in the wound site. The backing 72 may extend beyond the absorbent pad on all sides of the pad or the pad may completely cover the backing at one end of the dressing (as shown in FIG. 2b).

Figure 2C:
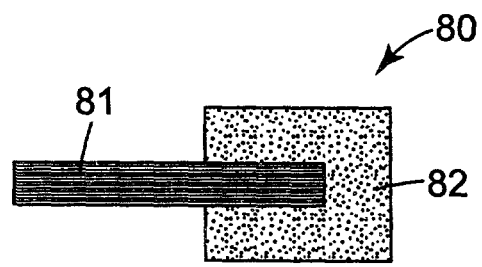

FIG. 2c illustrates a dressing 80 of the present invention that comprises a film backing 82 with adhesive surface; and fluid control film 81. The channels in the fluid control film 81 transport fluid from a covered wound site to a remote site.

Figure 2D:
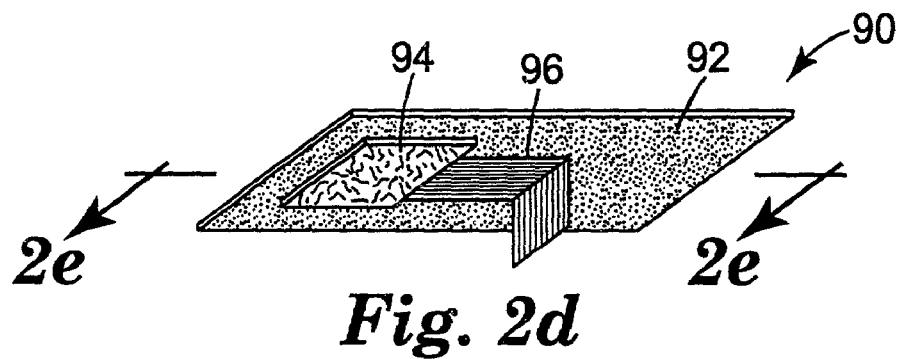
Figure 2E:
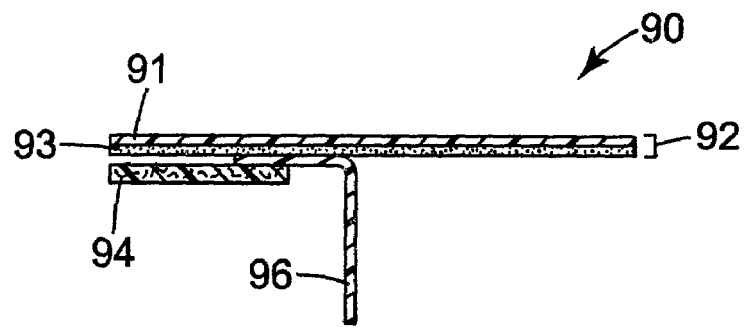
Figure 2F:
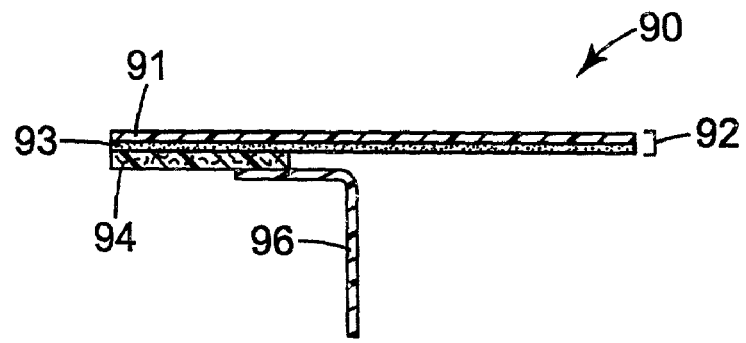

FIG. 2d illustrates a perspective view of a combined wound dressing and drain of the present invention. FIG. 2e illustrates a cross-sectional view of the dressing 90, taken along line 2e-2e. In this embodiment the dressing 90 comprises a backing 91 having an adhesive surface 93; an absorbent pad 94; and a fluid control film component 96 that transports fluid between a wound site and the absorbent pad 94. The fluid control film component of this embodiment may be bent away from the dressing and placed into a wound. In this manner the fluid control film component may be better able to drain the wound of excess fluid. If desired, the fluid control film could be extended past the edge of the dressing and the absorbent pad placed remote from the dressing. Also, in place of an absorbent pad it is contemplated that a suction device could be used to transport fluids to or from the wound site. FIG. 2*f* illustrates an alternative cross-sectional view of the dressing of FIG. 2*d*. In this embodiment the dressing 90 comprises a backing 91 having an adhesive surface 93; an absorbent pad 94; and a fluid control film component 96 that transports fluid between a wound site and the absorbent pad 94. In this embodiment the absorbent pad is placed between one end of the fluid control film 96 and the adhesive layer 93 of the dressing. In this embodiment, fluid control film 96 may be a separate component inserted in or applied to a wound surface, with dressing 90 subsequently applied.

FIG. 2*g* illustrates a bottom view of a perfusion bandage 84 of the present invention. In this embodiment fluid is provided under a dressing 85 from a reservoir 86 (shown schematically) using a fluid control film component 87. The fluid provided to the wound site from the reservoir may optionally contain a medicament (e.g., an antibiotic, antiseptic, steroid, growth factor, and the like). Excess fluid and wound exudate are optionally removed from the wound site using fluid control film 87 into a remote storage container 88 (e.g., an absorbent (such as a pad, gel, foam, and the like) or a reservoir of a suction device).

FIG. 2*h* illustrates yet a further alternative article 200 of the present invention. In this embodiment an adhesive layer 202 lies adjacent a portion of a fluid control film component 206. The channels of the fluid control film are effectively closed by the adhesive layer 202 but not occluded. An optional absorbent pad 204 may be placed adjacent a remote end of the fluid control film component. Alternatively, the remote end of the fluid control film component may be connected to a fluid source or suction device.

FIG. 2*i* illustrates a side view of a wound drain dressing of the present invention. The wound drain dressing 220 is shown with a conventional medical dressing 222 having backing 224 and adhesive layer 223. This dressing is adapted to be attached via adhesive layer 223 to the skin of a patient adjacent a wound site. An absorbent pad 225 is placed adjacent the backing of dressing 222 and held in place using any suitable means. In fluid communication with the absorbent pad is a length of fluid control film 226. The remote end 221 of the fluid control film is capable of being placed into a wound. Fluids are then transported between the wound and the pad 225. Tape 227 (having adhesive layer 228 and backing 229) may be utilized to secure fluid control film 226 and pad 225 to the dressing 222. This is only one suitable method of securing the components together. Adhesives, sonic welding techniques, etc. may be utilized in place of tape 227 if desired.

Wound drain 240 of FIG. 2*j* is comprised of a tubular piece of fluid transport film where in the microreplicated channels are on the inside of the tube. The tube may be formed from two pieces of fluid transport film sealed at the edges, as an extruded tube or in any other suitable manner. On the wound contact end 241 of the wound drain 240, part of the tube has been removed up to point 248 to expose microreplicated channels 242. In use, these channels are placed in fluid contact with the wound. Extending from edge 248 to edge 249 on one side of the wound drain 240 or around the entire circumference is coated a pressure sensitive adhesive 244. Adhesive 244 would be then covered with a removable protective release liner.

The wound drain 240 is applied by removing the liner and adhering adhesive section 244 to the wound site with channels 242 over the wound with at least a portion of channels 242 exposed to wound exudate. A dressing may then optionally be placed over the entire wound area and over the wound drain 240 from end 241 up to at least edge 249. Opening 246 can be placed in fluid communication with a vacuum source or adsorbent. For example, an absorbent could be placed inside the drain at or near opening 246.

As previously mentioned, the fluid control film component of the present invention may comprise multiple layers of microreplicated film in various configurations, including but not limited to: simple stacks of the fluid control film, laminated layers of the fluid control film forming closed capillaries between layers, as well as tubular configurations.

Certain multiple layer or tubular configurations of fluid control film can be used as components to transparent dressings such as apertured transparent dressings. For example, a tubular fluid wick could be formed with an absorbent core along part or all of a length that is inserted into an aperture or under the end of a dressing such as an adhesive coated transparent dressing.

Figure 3A:
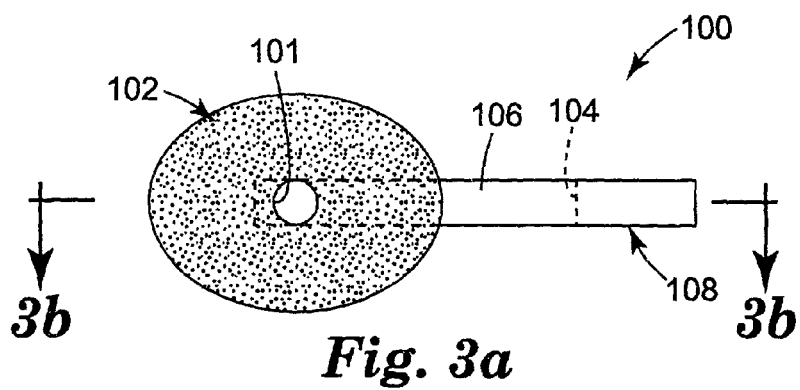
FIGS. 3a-3b illustrate a bottom view and cross-sectional view of a medical dressing of the present invention.
Figure 3B:
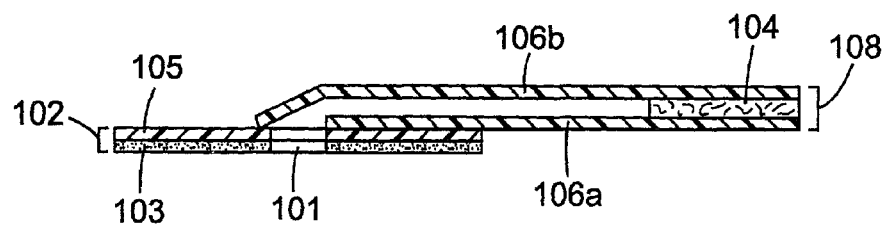

FIG. 3*a* and FIG. 3*b* illustrate bottom and cross-sectional views of a wound dressing 100 of the present invention. The dressing 100 includes medical dressing 102 (having backing 105 and adhesive layer 103); at least one aperture 101; and a fluid control film wick member 108 comprising a plurality of fluid control film (106*a* and 106*b* shown, though more layers could be used) and one or more absorbent pads 104. Fluid from the wound site leaves the site through aperture 101 and is transported by the wick member 108 to the absorbent.

In preferred embodiments, the fluid control film wick member lies flat and is sealed to the aperture by having the top layer extend over the opening as shown. Alternatively, a separate absorbent drain tube could be used by optionally adhesive coating the tip to allow placement followed by securing such as beneath a standard adhesive coated dressing.

In yet another embodiment, a fluid control film component could be used as a post surgical drain tube, wherein the microreplicated channels are on the interior of the tube, to allow for removal of wound exudate. In this application the drain tube may not be in communication with an absorbent but is rather hooked up to a vacuum source such as a vacuum pump or "HEMAVAC". Tubular drains may be formed directly by extrusion or from a film that is rolled into a tube and sealed or from two pieces of film optionally sealed at the edges. These drain tubes have certain advantages over a standard extruded tubular drain.

Preferred fluid control film drains of the present invention have low profile, producing less pain while employed and enabling the drain to be removed with less pain. In this design the structured fluid control film is designed to prevent occlusion as vacuum is applied. More preferred fluid control film drains can also remove gross fluids as done by current drain tubes while also removing fluid by capillary action. Certain embodiments may further comprise larger structures that serve to keep the tubular drain open to the desired degree. Finally, most preferred fluid control film drains may be made with linear fluid transport structures that have the capability of being ripped or torn linearly down the channel such that the end of a single drain tube could be split into multiple drains. In this manner, a single fluid control film drain could be used to replace multiple conventional drains.

As previously mentioned, in the wound dressing or wound drain embodiments of the present invention the microreplicated fluid transport channels may be present in the backing of the dressing, in the adhesive coating, or as a separate added insert.

Figure 3C:
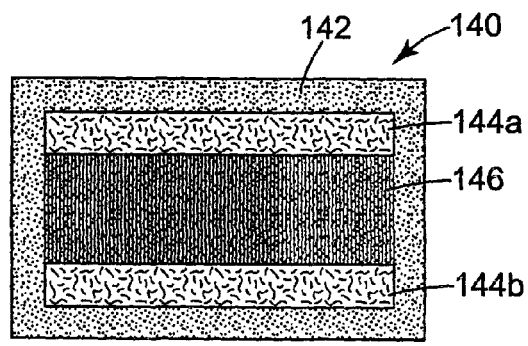
FIGS. 3c-3d illustrate additional medical dressings of the present invention.

As illustrated in FIG. 3c, a dressing 140 comprises a plurality of microreplicated channels in the adhesive layer of sheet 142. Absorbent regions (144a, 144b) may be used. Preferably, the absorbent regions are separated from the skin, e.g., using a layer of a suitable protective material such as MICRODON or DELNET.

In this embodiment excess wound exudate is transported off the wound (or an active agent could be delivered to a wound) by a microreplicated open capillary design formed into the adhesive itself. The adhesive is preferably non-flowable under zero shear, i.e. at rest, so that the pattern will remain intact during storage and while in use. This may be accomplished by crosslinking the adhesive through covalent bonds, ionic bonds, or through hydrogen bonding. For example, this may be achieved by crosslinking an acrylate adhesive with light, UV, heat, gamma or electron beam. Suitable adhesives of this type are disclosed in U.S. Pat. Nos. 5,225,473; 5,468,821 and 5,853,750. Alternatively, the adhesive can be a crosslinked polyurethane such as that disclosed in U.S. Pat. No. 5,591,820. An example, of suitable adhesives that can be crosslinked by hydrogen bonding in those disclosed in U.S. Pat. No. 4,871,812. The microreplicated fluid transport capillaries may be arranged in either or both major direction of the dressing or may be directed radially. Preferably the direction of the channels is across the dressing rather than down the dressing. This allows placement of the adhesive pads in a rotary converting operation without waste. Also, transport distance is minimized in this manner. Finally, the ends of the dressing are sealed, i.e. fluid cannot be wicked into the wound. In certain instances where it may be desirable to administer therapeutic agents to the wound the capillary channels may be turned 90 degrees such that they would run the length of the dressing. In this case, it may be necessary to seal the edges of the dressing with tape to prevent contamination from entering the wound from the exposed edges.

By making the capillary channels in the adhesive itself the cost of the dressing is minimized and the MVTR is maximized.

Figure 3D:
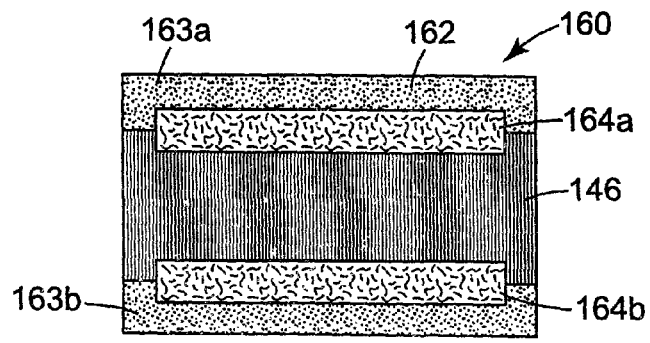

Alternatively, as illustrated in FIG. 3d, a dressing 160 comprises a plurality of microreplicated channels 146 in the backing layer of sheet 162. Absorbent regions (164a, 164b) may be used and may be separated from the skin during use by a suitable protective material (e.g., MICRODON or DELNET). Adhesive strips (163a, 163b) may be laid down on the lateral edges of the dressing. To form a complete seal around the entire dressing periphery, additional adhesive strips may be placed down across the other two edges of the dressing. Alternatively, the user could seal those edges with adhesive tape. The fluid transport capillaries travel at least up to and preferably over the absorbent to ensure the fluid is absorbed efficiently by the absorbent. To facilitate a fully automated manufacturing operation, the entire surface of the backing may be microreplicated, followed by a thermal nip applied only to the longitudinal edges immediately beneath and prior to placement of the adhesive. In this manner, the adhesive contact area is maximized. Alternatively, the adhesive could be simply placed over and occlude the microreplicated channels on the periphery of the dressing.

Figure 4A:
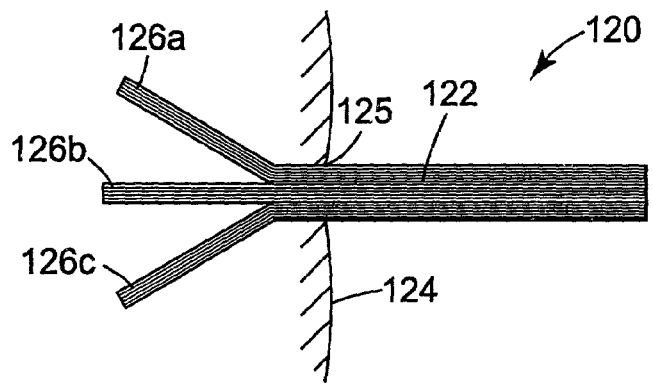
FIG. 4a illustrates a branched wound drain of the present invention.

FIG. 4a is a perspective view of a fluid control film drain 120 of the present invention. The drain 120 is shown partially inserted into a cavity 125 of a body surface 124. The inserted end of the fluid control film drain has been split into three branches 126a-c each of which is capable of transporting fluid by capillary action. Preferred drains of this type have channels that run the length of the drain and are configured to facilitate longitudinal tearing. In this manner, the drain may be easily split to drain multiple areas. The other end of the fluid control film tube may be attached to a vacuum source or in communication with an absorbent material. In this embodiment, the drain tube is held in place using, for example, a suture or skin staple placed directly in the drain or in a cuff around the drain as is common with conventional wound drains. Alternatively, an adhesive coated dressing or sealant may be used.

In another embodiment, the present invention provides a novel treatment for otitis media that utilizes novel tympanostomy wicks or tubes and/or a medicament (e.g., an antibacterial that can be coated on, incorporated in, or covalently attached to the article or placed in the inner ear by means of a syringe through the article itself). The novel wick or tube design utilizes microreplication to produce microchannels that transport fluid, e.g., by capillary action. Preferred designs also incorporate macrochannels to allow drainage of highly viscous fluid that cannot be removed by capillary forces. Suitable tympanostomy wicks or tubes incorporate a fluid control film as a fluid wick. Suitable films may be fabricated (e.g., by heat sealing or using adhesives) into preferred shapes and designs. Alternatively, a tube may be injection molded with microreplicated channels on the device itself. Furthermore, with an injection molded article the channels may be designed to have the fluid preferentially move in one direction, e.g. out of the ear, by having the channels tapered appropriately. The surface of the channels may be modified to make them hydrophilic as discussed herein.

Figure 5A:
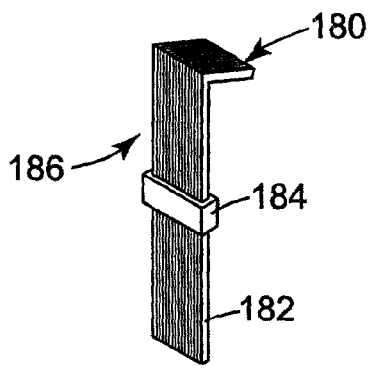
FIGS. 5a-5c illustrate tympanostomy wicks of the present invention.
Figure 5C:
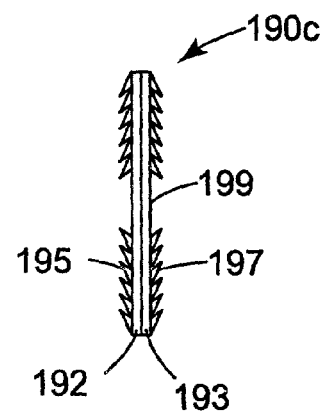
Figure 5B:
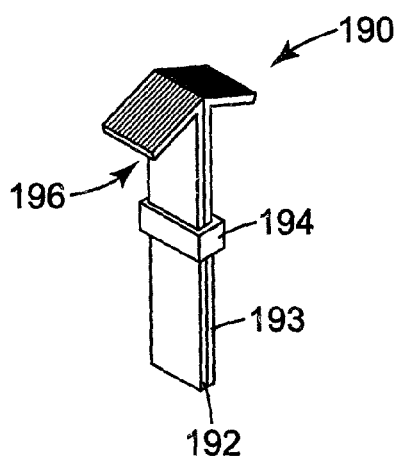

A further preferred aspect of the design is the collapsible umbrella-like end of the wick that prevents the wick from dislodging from the ear until the physician wishes it removed. As illustrated in FIG. 5a, the tympanostomy wick 180 comprises a strip of fluid control film component 182 and optional stop or collar 184 which serves to prevent the tube from going into the middle ear too far during insertion. As mentioned, the film 182 may be bent or folded 186 if desired. Also, fluid control film component 182 may comprise a single layer of fluid control film having channels on one of both surfaces) or may comprise a plurality of films in a stack. FIG. 5b illustrates a tympanostomy wick of the present invention comprising two strips of fluid control film component (192, 193), and optional stop or collar 194. Components 192, 193 may individually comprise one or more fluid control films. In this embodiment, components 192, 193 are bent away from each other at one end of the wick. The umbrella end is flexible enough to allow removal by the physician by forceps alone. It is anticipated that the function of stop (184, 194) may be achieved using molded projections or microstructure on the film. For example, as shown in FIG. 5c, a series of angled projections (195, 197) may be molded along the surface of the film to prevent the wick from dislodging from the ear. The angled projections may be angled toward an insertion point of the wick (199), thus allowing easy insertion of the wick to the desired depth and retention of the wick in both directions.

The fluid control film (wicks or tubes) optionally may be utilized to deliver a medicament to the inner ear. Suitable medicaments for this treatment include traditional antiseptics and antibiotics.

All references and publications cited herein are expressly incorporated herein by reference, in their entirely, into this disclosure. Particular embodiments of this invention will be discussed in detail in the examples below and reference has been made to possible variations to the particular embodiments that are within the scope of the invention. There are a variety of alternative techniques and procedures available to those skilled in the art that would similarly permit one to successfully practice the intended invention.

What is claimed is:

1. A medical treatment article comprising:
   at least one fluid control film component having at least one major surface, the major surface comprising a plurality of microreplicated channels that extends along the major surface and permits transport of fluid between a medical treatment site on a patient or user and a remote area;
   wherein the remote area comprises a fluid reservoir; and
   wherein the fluid control film component is adapted to supply a medicament from the fluid reservoir to the medical treatment site;
   wherein the fluid control film component comprises a plurality of primary channels having at least two secondary channels, each of the secondary channels forming at least one notch, wherein the primary channels have a depth of from 50 to 3000 microns and the depth of the secondary channels is from 5 to 50 percent of the depth of the primary channels.

2. A method of using a medical article comprising at least one fluid control film component having at least one microstructure-bearing surface with a plurality of microreplicated channels that extends along the surface and permits transport of fluid between a medical treatment site on a patient or user and a remote area, the method comprising:
   placing the medical article in proximity to the medical treatment site so that the fluid control film component is capable of providing fluid communication between the medical treatment site and the remote area; and
   allowing the medical treatment article to transport fluid between the medical treatment site and the remote area;
   wherein the fluid is transported from the remote area to the medical treatment site.

3. The method of claim 2 wherein fluid is transported from the medical treatment site to the remote area.

4. The method of claim 3 wherein the remote area comprises a fluid reservoir.

5. The method of claim 4 wherein the fluid reservoir comprises an absorbent material.

6. The method of claim 3 wherein the fluid comprises a medicament.

7. The method of claim 6 wherein the medicament comprises an antimicrobial, an antiseptic, an analgesic, a vitamin, a steroid, a growth factor, a nutrient, a flushing solution, or any combination of any of the foregoing.

8. The method of claim 2 further comprising visually observing the medical treatment site.

9. The method of claim 8 wherein at least a portion of the medical treatment article is transparent and the step of visually observing the medical treatment article comprises visually observing the medical treatment site through the transparent portion of the medical treatment article.

10. A method of using a medical article comprising at least one fluid control film component having at least one microstructure-bearing surface with a plurality of microreplicated channels that extends along the surface and permits transport of fluid between a medical treatment site on a patient or user and a remote area, the method comprising:
    placing the medical article in proximity to the medical treatment site so that the fluid control film component is capable of providing fluid communication between the medical treatment site and the remote area; and
    allowing the medical treatment article to transport fluid between the medical treatment site and the remote area;
    wherein fluid is transported from the medical treatment site to the remote area and from the remote area to the medical treatment site.

* * * * *